US009885653B1

(12) United States Patent
Buchtal et al.

(10) Patent No.: US 9,885,653 B1
(45) Date of Patent: Feb. 6, 2018

(54) DEVICE FOR THE ANALYSIS OF AN ANESTHESIA VENTILATION GAS AS WELL AS ANESTHESIA VENTILATOR

(71) Applicant: Drägerwerk AG & Co. KGaA, Lübeck (DE)

(72) Inventors: Ralf Buchtal, Lübeck (DE); Livio Fornasiero, Bliestorf (DE); Robert Jahns, Herrnburg (DE); Heike Vöhringer, Stuttgart (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 0 days.

(21) Appl. No.: 15/667,019

(22) Filed: Aug. 2, 2017

(30) Foreign Application Priority Data

Aug. 3, 2016 (DE) .................. 10 2016 009 366

(51) Int. Cl.
*G01J 5/00* (2006.01)
*G01N 21/3504* (2014.01)
(Continued)

(52) U.S. Cl.
CPC ....... *G01N 21/3504* (2013.01); *A61M 16/024* (2017.08); *A61M 16/085* (2014.02); *A61M 16/0833* (2014.02); *A61M 16/104* (2013.01); *A61M 16/12* (2013.01); *G01J 3/26* (2013.01); *A61M 2202/0241* (2013.01); *A61M 2205/3313* (2013.01); *A61M 2205/502* (2013.01); *A61M 2230/432* (2013.01); *G01N 2201/12* (2013.01)

(58) Field of Classification Search
CPC . G01N 21/3504; G01N 2201/12; G01N 21/00
USPC .................................................. 250/339.13
See application file for complete search history.

(56) References Cited

U.S. PATENT DOCUMENTS

2012/0097852 A1* 4/2012 Weckstrom .......... G01N 21/314
250/343

FOREIGN PATENT DOCUMENTS

DE         101 40 998 C2    7/2003
DE    10 2009 011 421 B3    4/2010

OTHER PUBLICATIONS

Li, Yun-Long, Yang, Bing-Chu, Xu, Xue-Mei: Wavelength modulation spectroscopy at ( . . . ), Chin. Phys. B vol. 25, 2016 No. 2; p. 024208-1-024208-5.

* cited by examiner

*Primary Examiner* — David Porta
*Assistant Examiner* — Meenakshi Sahu
(74) *Attorney, Agent, or Firm* — McGlew and Tuttle, P.C.

(57) ABSTRACT

A device analyzes an anesthesia ventilation gas with an infrared radiation source and includes a gas cuvette, a Fabry-Perot interferometer with a band pass filter function, adjustable with respect to a central transmission wavelength as a function of a control signal, a detector providing a measured signal and a computing and control unit providing the control signal and detecting the measured signal. The computing and control unit is configured to actuate the Fabry-Perot interferometer in a first operating mode by the control signal such that the central transmission wavelength scans a predefined wavelength range, to detect a presence in the ventilation gas sample potential types of anesthetic gases based on the measured signal. In a second operating mode, the control unit controls the central transmission wavelength within a subrange of the predefined wavelength range and determines a plurality of concentration values at consecutive times for detected types of anesthetic gases.

20 Claims, 18 Drawing Sheets

(51) Int. Cl.
*G01J 3/26* (2006.01)
*A61M 16/10* (2006.01)
*A61M 16/12* (2006.01)
*A61M 16/08* (2006.01)
*A61M 16/00* (2006.01)

FIG. 9

| {G1}     | {UB1} |
|----------|-------|
| {G1, G2} | {UB2} |
| {G1, G3} | {UB3} |
| {G2}     | {UB4} |
| {G2, G3} | {UB5} |
| {G3}     | {UB6} |
| ⋮        | ⋮     |
|          | {UBK} |

DUB k ↓

DEVICE FOR THE ANALYSIS OF AN ANESTHESIA VENTILATION GAS AS WELL AS ANESTHESIA VENTILATOR

CROSS REFERENCE TO RELATED APPLICATIONS

This application claims the benefit of priority under 35 U.S.C. § 119 of German Application 10 2016 009 366.8 filed Aug. 3, 2016, the entire contents of which are incorporated herein by reference.

FIELD OF THE INVENTION

The invention relates to a device that analyzes an anesthesia ventilation gas with an infrared radiation source and includes a gas cuvette arranged in a measuring path for receiving a ventilation gas sample of the anesthesia ventilation gas and further relates to an anesthesia ventilator (also known as an anesthesia respirator) with such as device.

BACKGROUND OF THE INVENTION

The anesthetic gas components and the types of anesthetic gas that are contained in an anesthesia ventilation gas and the respective percentages at which these are contained in the anesthesia ventilation gas fed to the patient and in the gas exhaled by the patient represent essential information for an anesthesiologist in the course of the anesthesia of a patient. Examples of types of anesthetic gas are, e.g., fluranes, such as desflurane, isoflurane or sevoflurane.

A determination of the particular concentrations of respective types of anesthetic gas is performed here according to the state of the art optically on the basis of a determination of the absorption of optical radiation of certain wavelengths.

The goal is a selective determination of the individual percentages and respective concentrations in an anesthesia ventilation gas, which represents a gas mixture. Devices for such a gas analysis according to the state of the art sometimes have a complicated configuration or it is expensive to manufacture them.

A device for identifying and determining the concentrations of different gas components in an anesthesia ventilation gas, in which radiation components of different wavelengths are transmitted to respective different detectors through a gas cuvette and wherein a respective detector and a respective filter associated with the detector are further used for each particular wavelength, is known from DE 101 40 998 C2. Consequently, a so-called filter bank must be built up in order to measure respective absorptions in the anesthesia ventilation gas at different wavelengths. Such a filter bank is at times so complex that the corresponding configuration requires a certain minimum volume.

The configuration of the filter bank mentioned may also be considered to be an arrangement of a plurality of partial cuvettes connected pneumatically in series with a multichannel detector, wherein the cuvette volumes adding up determine the minimum volume. This minimum volume possibly only permits an inaccurate determination of the concentration in case of abrupt changes in the concentrations of the gas components, because the corresponding pneumatic time constant associated therewith may become relatively high.

Other analyzers for absorption analysis utilize, e.g., a filter wheel in front of a detector, which filter wheel filters out a particular wavelength according to the particular position, and the filter wheel must then be rotated to change the wavelength reaching the detector. It is consequently possible hereby to bring about a change in the wavelength as viewed by the detector, in the sense of a scan, over a certain wavelength range. The drawback is, however, that the filter wheel is subject to a certain wear.

The measurement method known, in principle, from the state of the art for determining a concentration of an individual gas component as part of a gas mixture on the basis of at least two wavelengths will now be explained first in general terms for a better understanding by the reader. An optical signal, preferably infrared radiation, of at least one first wavelength and of at least one additional wavelength is radiated into a volume to be monitored for the gas component or into a gas cuvette to be monitored for measuring a concentration of an individual gas component.

The first wavelength is selected to be such that radiation of this first wavelength through the gas component, whose concentration shall be determined, is absorbed. Such an absorbance can be described by the Beer-Lambert law. A received intensity of the radiation of the first wavelength is then detected by means of a detector located behind the gas cuvette. An indicator of the absorbance of the radiation of the first wavelength can then be inferred from the knowledge of the intensity transmitted at the radiation source at the first wavelength as well as of the intensity measured at the detector. The first wavelength is also called the measuring wavelength.

However, since the radiation of the first wavelength is possibly absorbed not only by the gas component itself, but, for example, also by other effects, such as a contamination of the detector, moisture or condensate present in the gas mixture, or other effects, e.g., aging of the radiation source, the additional wavelength is selected, further, to be such that the radiation of the additional wavelength is not absorbed by the gas component but nevertheless on the basis of the other effects. This additional wavelength is also called reference wavelength. A received intensity can then also be detected for the radiation of the additional wavelength by means of an additional detector located behind the gas cuvette.

An indicator of an absorbance by the gas component in the gas mixture can then be inferred by means of the measured or detected intensities at the two different wavelengths. Taking the Beer-Lambert law into account, the concentration of a gas component in the gas mixture can then be inferred from the absorbance, with simultaneous compensation of the other above-mentioned effects.

The principle of measurement described based on the state of the art can then be used if an absorbance by only a certain gas component or by a particular type of anesthetic gas is to be expected at a first wavelength. However, since it may happen that plurality of gas components or a plurality of types of anesthetic gas may be present in the gas mixture or in the anesthesia ventilation gas, absorbance by a first type of anesthetic gas as well as by a second type of anesthetic gas may occur at the first wavelength. An accurate determination of a first concentration of the first type of anesthetic gas and of a second concentration of the second type of anesthetic gas now requires the determination of an absorbance not only at the first wavelength, but, for example, at three different measuring wavelengths within a wavelength range. The aforementioned additional reference wavelength must likewise be used now for an absorbance measurement, because the effects mentioned shall be compensated during such a measurement as well.

Both the first concentration of the first type of anesthetic gas and the second concentration of the second type of anesthetic gas can then be determined on the basis of such four wavelengths for the particular absorbance measurement.

FIG. 1 shows exemplary absorbance coefficients in a range of values between 0 and 1 for wavelengths in the μm range in the presence of the exemplary type of anesthetic gas halothane or of the exemplary type of anesthetic gas enflurane. The respective absorbance curves KV1 for enflurane as well as KV2 for halothane can be recorded for a defined configuration of a gas and for an exemplary partial pressure, in this case a partial pressure of 50 mbar, as well as for a defined temperature during a reference measurement to be performed beforehand and acquired in a data set. For example, three wavelengths $\lambda 1$, $\lambda 2$, $\lambda 3$ are entered here, which may be suitable for a combined measurement of halothane and enflurane. Further, the reference wavelength $\lambda R$ is entered with 10.5 μm, because essentially no absorbance by halothane or enflurane occurs at this wavelength $\lambda R$.

FIG. 2 shows additional exemplary absorbance curves KV3, KV4, KV5, which were recorded for the respective fluranes desflurane (curve K4), isoflurane (curve K5) or sevoflurane (curve K3) in a gas cuvette within the framework of a reference measurement or measurement example.

SUMMARY OF THE INVENTION

According to the invention, a device is provided for the analysis of an anesthesia ventilation gas. The device has at least one infrared radiation source for the emission of an infrared radiation along a measuring path; at least one gas cuvette arranged in the measuring path for receiving a ventilation gas sample of the anesthesia ventilation gas; a Fabry-Perot interferometer arranged in the measuring path with a band pass filter function (band pass filter means), which can be adjusted in respect to its central transmission wavelength as a function of a control signal; at least one detector arranged at one end of the measuring path for providing a measured signal, which indicates an infrared radiation intensity transmitted through the gas cuvette and through the band pass filter function of the Fabry-Perot interferometer; as well as at least one computing and control unit for providing the control signal and, further, for detecting the measured signal. Further, the computing and control unit is configured to actuate the Fabry-Perot interferometer in a first operating mode by means of the control signal such that the central transmission wavelength scans over a predefined wavelength range and further to detect a respective presence in the ventilation gas sample on the basis of the measured signal for the respective, potential types of anesthetic gas. The computing and control unit is further configured to actuate the Fabry-Perot interferometer by means of the control signal in a second operating mode such that the central transmission wavelength corresponds to a preferred wavelength or to a plurality of preferred wavelengths within a subrange of the predefined wavelength range, wherein the computing and control unit selects as a function of the types of anesthetic gas that were detected in the first operating mode as being present, and further to determine a plurality of respective concentration values at consecutively following times on the basis of the measured signal for the respective types of anesthetic gas detected as being present.

The advantageous mode of operation of the device for the analysis of an anesthesia ventilation gas will now be explained in more detail.

Different, individual types of anesthetic gases or different combinations of types of anesthetic gases may occur during different phases of anesthesia within the framework of anesthesia ventilation. An anesthesiologist may select a first type of anesthetic gas, e.g., for a so-called induction phase and then change over to another type of anesthetic gas later. A phase during which both types of anesthetic gas may be present may occur during the changeover. Therefore, the anesthetic gas-measuring device does not necessarily know what kinds of types of anesthetic gas are present in the anesthesia ventilation gas, because this depends on the selection made by the anesthesiologist or it depends on the phase of the anesthesia ventilation. The presence of no type of anesthetic gas, the presence of an individual type of anesthetic gas or else the presence of a combination of two types of anesthetic gas is usually to be expected within the framework of the anesthesia ventilation of a patient depending on the phase of this anesthesia ventilation. Different binary combinations of types of anesthetic gases must therefore be able to be measured in respect to their respective concentrations. Consequently, if an anesthetic gas-measuring device shall be able to perform a concentration measurement for different combinations of the five types of anesthetic gas shown in FIGS. 1 and 2, it is sometimes insufficient to have the measuring wavelengths $\lambda 1$, $\lambda 2$, $\lambda 3$ from FIG. 1 as fixed wavelengths in respect to the two types of anesthetic gas shown there for the absorbance measurement, because these measuring wavelengths could be unsuitable, for example, for a measurement of one or more types of anesthetic gas from FIG. 2. Especially wavelength $\lambda 2$, which is also shown in FIG. 2, would be absorbed especially strongly by desflurane, so that the measuring accuracy could be greatly reduced. It may therefore be necessary for a concentration measurement by means of absorbance measurement to scan a wavelength range of, e.g., 7 μm to 11 μm if different types of anesthetic gases are potentially present and then to select from these scanned wavelengths defined respective tuples with three determined measuring wavelengths, which are advantageous for respective defined combinations of types of anesthetic gases in respect to an absorbance measurement. A scanning or sweeping of different tuples or combinations of measuring wavelengths is carried out according to the present invention in the first operating mode by scanning the central transmission wavelength of the band pass filter function of the Fabry-Perot interferometer over the predefined wavelength range.

Further, it is not only necessary within the framework of an anesthesia situation for an anesthesiologist to know respective concentrations of respective different types of anesthetic gases in the anesthesia ventilation gas per se. The respective concentrations shall sometimes also be made available to the anesthesiologist with the great possible temporal resolution, because the anesthesiologist could possibly infer the state of the patient from a precise time course of one or more concentrations. Such information is known, for example, through a representation of so-called capnograms within the framework of a ventilation, such capnograms showing to the anesthesiologist a carbon dioxide content in the breathing gas with a high temporal resolution, so that a very precise course of the carbon is represented for the anesthesiologist over time during a single breath.

Due to the fact that the device scans a predefined wavelength range in the first operating mode, such a wavelength range may be suitable for detecting different respective potential types of anesthetic gas per se. As was already mentioned before in reference to FIGS. 1 and 2, one or more measuring wavelengths must be varied over a broader spectral range or wavelength range in order to be able to detect the presence of different types of anesthetic gases with certainty. Even though a measurement is possible, in principle, at greatly different wavelengths in this range between 7 µm and 11 µm by means of such a scanning over the central transmission wavelength over the predefined wavelength range to record fitting measured absorbance values for the different types of anesthetic gases at advantageous wavelengths, this nevertheless implies one drawback: New measured absorbance values can only be recorded after scanning over the predefined wavelength range again in order to then determine new concentration values. Consequently, if the scan over the predefined wavelength range in the first operating mode has a certain minimum duration, new measured values can only be recorded at different wavelengths after the end of this minimum duration for determining new concentration values for the respective types of anesthetic gases. Thus, this minimum duration of the scan over the predefined wavelength range determines the temporal resolution of the recording of the concentration values of the types of anesthetic gases during the first operating mode.

Due to the fact that the computing and control unit varies the central transmission wavelength of the band pass filter function by means of the control signal in the second operating mode such that the transmission to a preferred wavelength or to a plurality of preferred wavelengths within a subrange of the predefined wavelength range, a variation of the measuring wavelength in the subrange can be performed within a duration that is shorter than the minimum duration for scanning over the predefined wavelength range during the first operating mode, because the subrange is smaller than the predefined wavelength range. The computing and control unit now selects the subrange for the central transmission wavelength as a function of the types of anesthetic gases whose presence was detected in the first operating mode. Consequently, the subrange is selected in an intelligent manner such that a measurement only takes place in such a subrange that is necessary in the first place for a concentration measurement of the types of anesthetic gas actually detected in the first operating mode. As a result, the times consecutively following one another, at which a plurality of concentration values were determined in the second operating mode on the basis of the measured signal for the respective types of anesthetic gases detected as being present, can consequently be selected with a higher temporal resolution than this would be the case if a concentration value measurement were always carried out in the manner that, as it takes place in the first operating mode, the entire predefined wavelength range were swept over with the corresponding minimum duration in time.

In other words, the concentration measurement of a type of anesthetic gas or of a plurality of types of anesthetic gases is possible in the first operating mode with a first temporal resolution, whereas a concentration measurement of a type of anesthetic gas or of a plurality of types of anesthetic gases is possible in the second operating mode with a second temporal resolution, the second temporal resolution being higher than the first temporal resolution.

The central transmission wavelength is preferably limited to the selected subrange in the second operating mode.

The computing and control unit consequently preferably selects the subrange as a function of either a type of anesthetic gas detected as being present or, if a plurality of types of anesthetic gases were detected, as a function of the plurality of types of anesthetic gases detected as being present.

Likewise, the determination of a plurality of respective concentration values is preferably only performed for such types of anesthetics whose presence was actually detected in the first operating mode.

The wavelength range predefined for the first operating mode is preferably within a wavelength range from 7 µm to 11 µm, and the predefined wavelength range does not have to fully cover the wavelength range. This means that the entire wavelength range from 7 µm to 11 µm does not have to be covered by the predefined wavelength range, and it is sufficient for the predefined wavelength range to be located between these limits of 7 µm and 11 µm.

The computing and control unit preferably selects the one preferred wavelength or the plurality of preferred wavelengths as a function of the types of anesthetic gases detected as being present. It becomes possible as a result to adjust the preferred wavelengths actually used for the measurement or the preferred wavelength to the detection result from the first operating mode. If, for example, only a single type of anesthetic gas was detected in the first operating mode, a measurement at an individual preferred measuring wavelength may be sufficient in the second operating mode. A measurement result from the first operating mode may be used here for the reference wavelength. If two types of anesthetic gas were detected in the first operating mode, three preferred measuring wavelengths may preferably be used in the second operating mode. A measurement result from the first operating mode may now be used for the reference wavelength, because the effect to be compensated is subject to a relatively slow change over time only.

At least some of the types of anesthetic gases are preferably fluranes.

The device is preferably configured such that the predefined wavelength range, which scans over the central transmission wavelength in the first operating mode, has at least a partial range of 8 µm to 9 µm. This partial range is advantageous, because essential absorbance effects are to be expected between 8 µm and 9 µm due to frequently used types of anesthetic gases.

The device is preferably configured such that the computing and control unit selects a preferred wavelength or the plurality of preferred wavelengths as a function of a data set, which indicates respective wavelength combinations or respective subranges for respective combinations of types of anesthetic gases. This is advantageous, because the respective wavelength combinations or respective subranges indicated in the data set can be selected in an automated manner as a function of respective types of anesthetic gases detected as being present in the second operating mode.

The device is preferably configured such that the computing and control unit selects a preferred wavelength or the plurality of preferred wavelengths such that a type of anesthetic gas detected as being present has a predefined minimum amount of energy absorption of the infrared radiation at at least one of the preferred wavelengths. This is advantageous because a minimum absorbance can also only be measured in case of a minimum amount of energy absorption at a preferred wavelength.

The device is preferably configured such that the Fabry-Perot interferometer has a plurality of band pass filter functions of different orders, as well as that the band pass filter function is a first band pass filter function of a first type order with the central transmission wavelength as a first central transmission wavelength; that an additional band pass filter function is a second band pass filter function of a second type order with a second central transmission wavelength; that the detector is a first detector, which is configured for providing a first measured signal, which indicates a first intensity of the infrared radiation, which intensity was transmitted through the gas cuvette and through the first band pass filter function; and that the device further has a second detector, which is arranged at the end of the measuring path and which is configured for providing a second measured signal, which indicates a second intensity of the infrared radiation, which intensity was transmitted through the gas cuvette and through the second band pass filter function of the Fabry-Perot interferometer. Further, the computing and control unit is configured to actuate the Fabry-Perot interferometer in the operating mode by means of the control signal such that the second central transmission wavelength corresponds at least at times to an additional preferred wavelength between 4 µm and 5 µm and to determine a plurality of concentration values at a plurality of consecutively following times on the basis of the second measured signal for carbon dioxide. This configuration of the present invention is advantageous because, on the one hand, this configuration can be used for an anesthetic gas measurement in a first wavelength range, e.g., above 7 µm, by means of the first band pass filter function of the first type order and by means of the first detector at the preferred wavelengths, and because, on the other hand, this configuration can be used for a measurement of concentration values for carbon dioxide in a wavelength range between 4 µm and 5 µm by means of the second band pass filter function of the second type order and by means of the second detector. It is not necessary now to provide a separate, fixed optical filter with a fixed, narrow-band transmission wavelength for the measurement of the carbon dioxide concentration, but the second band pass filter function of the second-type order of the Fabry-Perot interferometer can be used for this carbon dioxide measurement. Such a measurement of carbon dioxide is also possible now for at least some times during the first operating mode.

The device is preferably configured such that it further has at least one fixed optical filter, which has a fixed band pass filter function with a fixed central transmission wavelength between 4 µm and 5 µm, the detector being a first detector, which is configured for providing a first measured signal, which indicates an intensity of the infrared radiation, which intensity was transmitted through the gas cuvette and through the band pass filter function of the Fabry-Perot interferometer, wherein the device further has a second detector, which is arranged at the end of the measuring path and which is configured for providing a second measured signal, which indicates a second intensity of the infrared radiation, which intensity was transmitted through the gas cuvette and through the fixed band pass filter function of the fixed optical filter. The computing and control unit is configured here such that, further, a plurality of concentration values are determined at a plurality of times following one another on the basis of the second measured signal for carbon dioxide at least in the second operating mode. This configuration of the device is advantageous, because a carbon dioxide concentration measurement can be performed by means of the fixed optical filter at the same time simultaneously with the anesthetic gas measurement performed by means of the Fabry-Perot interferometer.

The device is preferably configured such that the device further has a data interface, wherein the computing and control unit is configured to provide the concentration values at the data interface. This configuration is advantageous, because it makes it possible to provide the concentration values in the form of a data signal for additional devices.

The device is preferably configured such that the device further has a gas port for the supply of the ventilation gas sample of the anesthesia ventilation gas. This configuration is advantageous, because the device can be connected hereby, for example, to a measured gas line of an anesthesia ventilator.

The device is preferably configured such that the gas port is configured for connection to a Y-piece of a ventilation tube. This configuration is advantageous, because a measurement is now possible in the vicinity of the Y-piece, so that the measuring accuracy relative to an exhaled gas of a patient is increased.

The device is preferably configured such that the computing and control unit is configured to change over from the second operating mode back into the first operating mode no later than after the end of a maximum duration of the second operating mode. This configuration is advantageous because the operation is changed back over again into the first operating mode after the end of the minimum duration in order to detect a possibly changed composition of the anesthesia ventilation gas due to different types of anesthetic gas.

The device is preferably configured such that the computing and control unit is configured to receive input data of an input unit and further to select the maximum duration of the second operating mode as a function of the input data. This embodiment is advantageous, because an anesthesiologist can determine himself, by presetting the input data, how often a testing of the composition of the anesthesia ventilation gas consisting of different types of anesthetic gases is performed by the device in the first operating mode. The patient is possibly in an anesthesia phase of the anesthesia ventilation, during which the anesthesiologist does not expect any change or any essential change in the composition of the anesthesia ventilation gas. By making corresponding inputs, he can then increase the duration of the second operating mode, in which the temporal resolution of the concentration value determination is lower than in the second operating mode.

The device is preferably configured such that the computing and control unit is configured to modulate the amplitude of the infrared radiation source according to a modulation frequency in the second operating mode by means of an additional control signal, wherein the computing and control unit selects the modulation frequency as a function of the types of anesthetic gas detected as being present from the first operating mode. This configuration is advantageous, because interference effects due to equisignal components can be reduced by means of an amplitude modulation of the infrared radiation source and a lock-in analysis of the measured signal by means of a lock-in amplifier on the detector side. If an amplitude modulation of the infrared radiation source is carried out with a certain modulation frequency, this modulation frequency must be selected to be high enough for a minimum number of signal periods to reach the detector at a certain measuring wavelength or central wavelength of the band pass filter function; if the central transmission wavelength is changed over time, as it happens in the first operating mode due to the scan over the predefined wavelength range, this corresponds to a frequency change or frequency modulation of the central wavelength. The greater the change over time in the central wavelength, the greater is the corresponding frequency modulation and the higher must be the frequency of the amplitude modulation of the infrared radiation source. For example, a measurement may only be necessary at a single wavelength in the case in which only a single type of anesthetic gas was detected in the first operating mode, and the modulation frequency can then be selected at a lower value at this measuring wavelength than when then central transmission wavelength is changed greatly over time for scanning three wavelengths, which would require a higher modulation frequency for the amplitude modulation of the radiation source. The lower the modulation frequency for the amplitude modulation, the greater will be the signal-to-noise ratio of the detected or received signal at the detector. Consequently, if only one measuring wavelength or only one central transmission wavelength is necessary for only one detected type of anesthetic gas, the modulation frequency for the amplitude modulation can then be selected to be lower than when a change is necessary over time in the central transmission wavelength for the measurement at different measuring wavelengths for a plurality of types of anesthetic gases.

An anesthesia ventilation with a device for analyzing an anesthesia ventilation gas according to the present invention is further proposed.

Further, an anesthesia ventilator with a computing and control unit for the analysis of an anesthesia ventilation gas is proposed, wherein the computing and control unit is configured for providing a control signal and further for detecting a measured signal, wherein the computing and control unit is further configured to actuate a Fabry-Perot interferometer by means of the control signal in a first operating mode such that a central transmission wavelength of a band pass filter function of the Fabry-Perot interferometer scans over a predefined wavelength range as well as further to detect a respective presence of respective, potential types of anesthetic gas in the ventilation gas sample on the basis of the measured signal. Further, the computing and control unit is configured to actuate the Fabry-Perot interferometer in a second operating mode by means of the control signal such that the central transmission wavelength corresponds to a preferred wavelength or to a plurality of preferred wavelengths within a subrange of the predefined wavelength range, wherein the computing and control unit selects the subrange as a function of types of anesthetic gas detected as being present, and it determines a plurality of respective concentration values at a plurality of times following one another on the basis of the measured signal for the respective types of anesthetic gas detected as being present.

The present invention will be explained in more detail below on the basis of figures based on special embodiments without limitation of the general inventive idea. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 9 is a diagram showing a data set, which indicates respective preferred wavelength combinations for respective combinations of types of gas;

DESCRIPTION OF THE PREFERRED EMBODIMENTS

Figure 4:
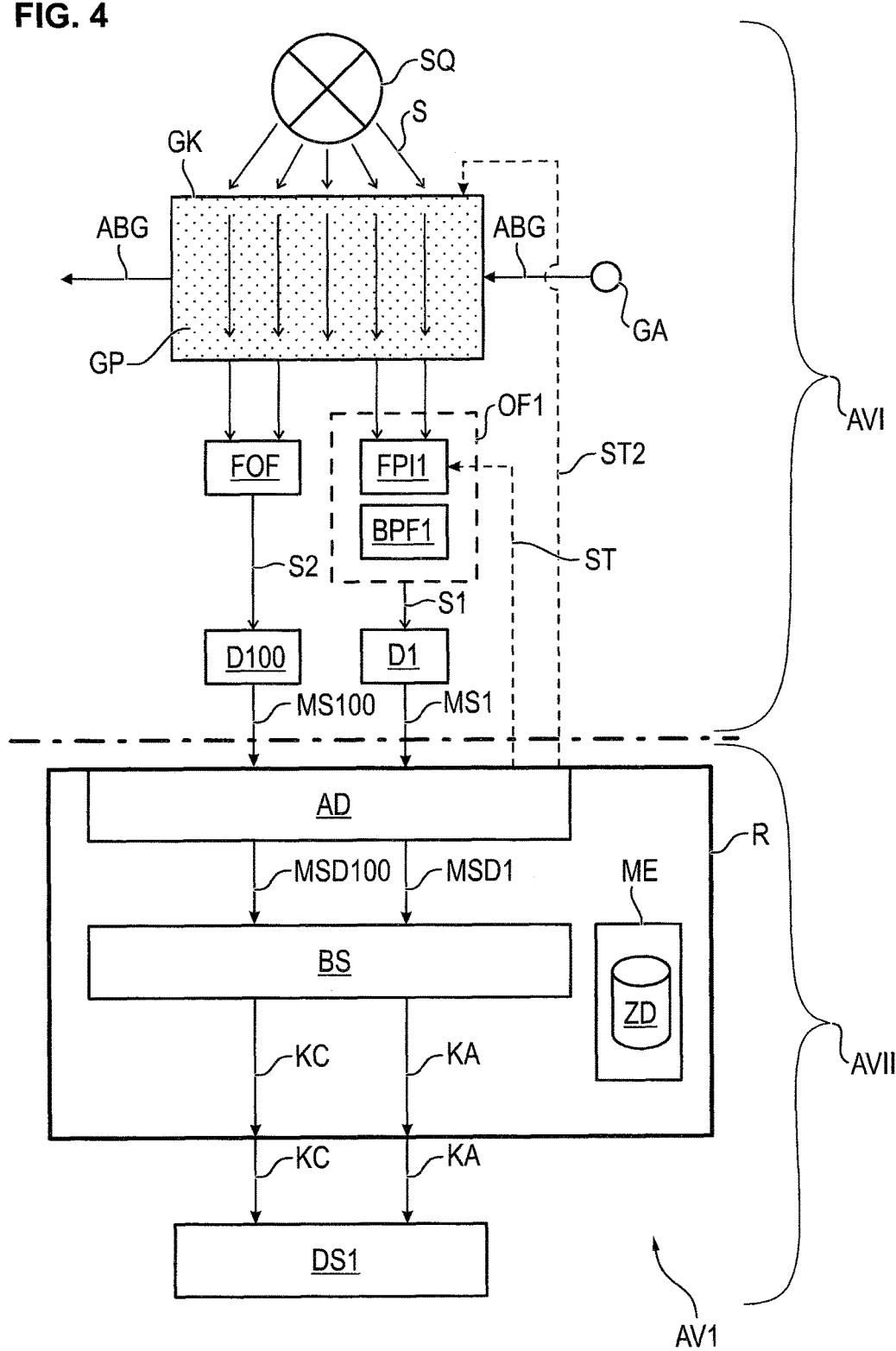
FIG. 4 is a schematic view of a first preferred embodiment of the device according to the present invention.

Referring to the drawings, FIG. 4 shows a preferred embodiment AV1 of the device according to the present invention for the analysis of an anesthesia ventilation gas ABG.

The device AV1 has an infrared radiation source SQ for the emission of infrared radiation S along a measuring path between the radiation source SQ and at least one detector D1.

At least one gas cuvette GK, which is configured for receiving a ventilation gas GP of the anesthesia ventilation gas ABG, is arranged in the measuring path. The anesthesia ventilation gas ABG is preferably received by the device AV1 via a gas port GA and is sent to the cuvette GK. Further, a Fabry-Perot interferometer FPI1, which has at least one band pass filter function (band pass filter or band pass filter means) is located in the measuring path.

Figure 7:
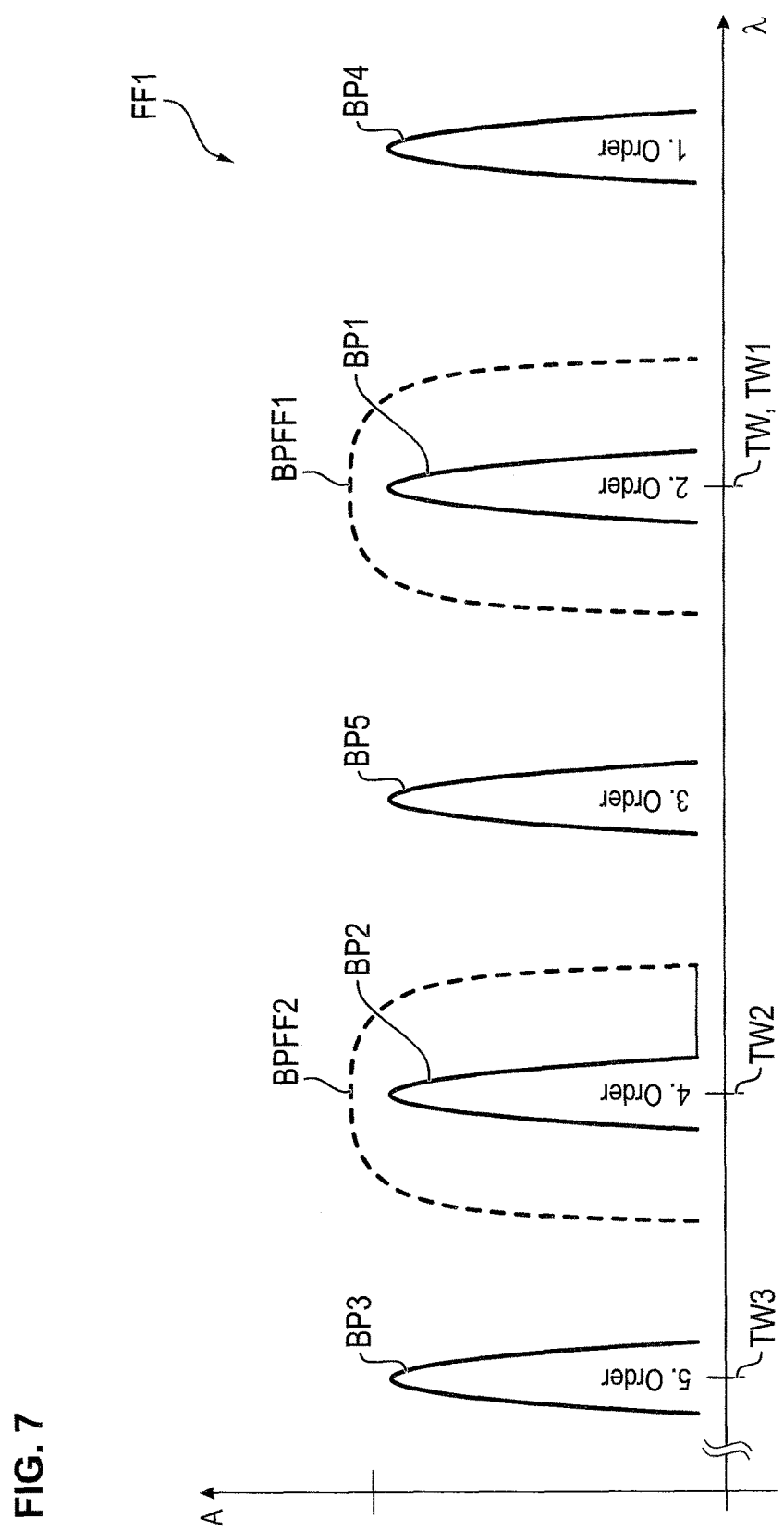
FIG. 7 is a diagram showing exemplary band pass filter functions of a Fabry-Perot interferometer.

FIG. 7 shows for this as an example a transfer function FF1 of a Fabry-Perot interferometer FPI1, which has a plurality of band pass filter functions BP1, . . . , BP5 of different orders with a varying amplitude A over the wavelength $\lambda$. One of the band pass filter functions BP1 has a central transmission wavelength TW, which corresponds to a center frequency of the band pass filter function BP1. The band pass filter function BP1 is preferably a second-order band pass filter function of the Fabry-Perot interferometer.

Additional fixed band pass filter functions BPFF1, BPFF2, which belong to corresponding additional fixed band pass filters, which are not part of the Fabry-Perot interferometer, can be used to filter out one of the band pass filter functions BP1, . . . , BP5 of the Fabry-Perot interferometer. These fixed band pass filters will be discussed in more detail later.

According to FIG. 4, at least one detector D1, which provides a measured signal MS1, is arranged at the end of the measuring path. The detector D1 is preferably an optical detector, especially a pyroelectric detector. An additional fixed band pass filter BPF1 is located, together with the Fabry-Perot interferometer FPI1, in the measuring path between the detector D1 and the radiation source SQ. With the fixed band pass filter function, see function BPFF1 from FIG. 7, the additional band pass filter BPF1 filters out a band pass filter function of a certain order of the Fabry-Perot interferometer FPI1, see function BP1 from FIG. 7. The Fabry-Perot interferometer FPI1 and the fixed band pass filter BPF1 may also be configured as a common optical device OF1.

The detector D1 provides such a measured signal MS1 which indicates an intensity S1 of the infrared radiation S, which intensity was transmitted through the gas cuvette GK and through the band pass filter function of the Fabry-Perot interferometer FPI1. In other words, the digital measured signal MSD1 indicates an intensity S1 of the infrared radiation S, which intensity was transmitted through the gas cuvette GK, through the band pass filter function of the Fabry-Perot interferometer FPI1 and through the band pass filter function of the fixed band pass filter BPF1.

The device AV1 further has at least one computing and control unit R for providing at least one control signal ST as well as for detecting at least one measured signal MS1.

The measured signal MS1 is converted by an analog/digital converter AD of the computing unit R into a digital representation or a digital measured signal MSD1. Consequently, this digital signal MSD1 can thus also be considered to be the measured signal of the detector D1.

The computing unit R detects the presence of respective, potential types of anesthetic gas in the ventilation gas sample GP in a first operating mode by means of a determination step BS and it further determines a plurality of respective concentration values at times following one another for the respective types of anesthetic gas detected as being present in a second operating mode.

The individual detail steps of the determination step BS for carrying out the first operating mode and the second operating mode are carried out by the computing unit R with the aid of a memory unit ME, which contains assignment data ZD, which will be discussed in more detail below.

The plurality of respective concentration values for the respective types of anesthetic gas detected as being present are then provided by the computing unit R as a set of concentration values or as a data set of concentration values KA, preferably at a data interface DS1.

The device AV1 can thus be divided into a first partial device AVI and a second partial device AVII.

Figure 6:
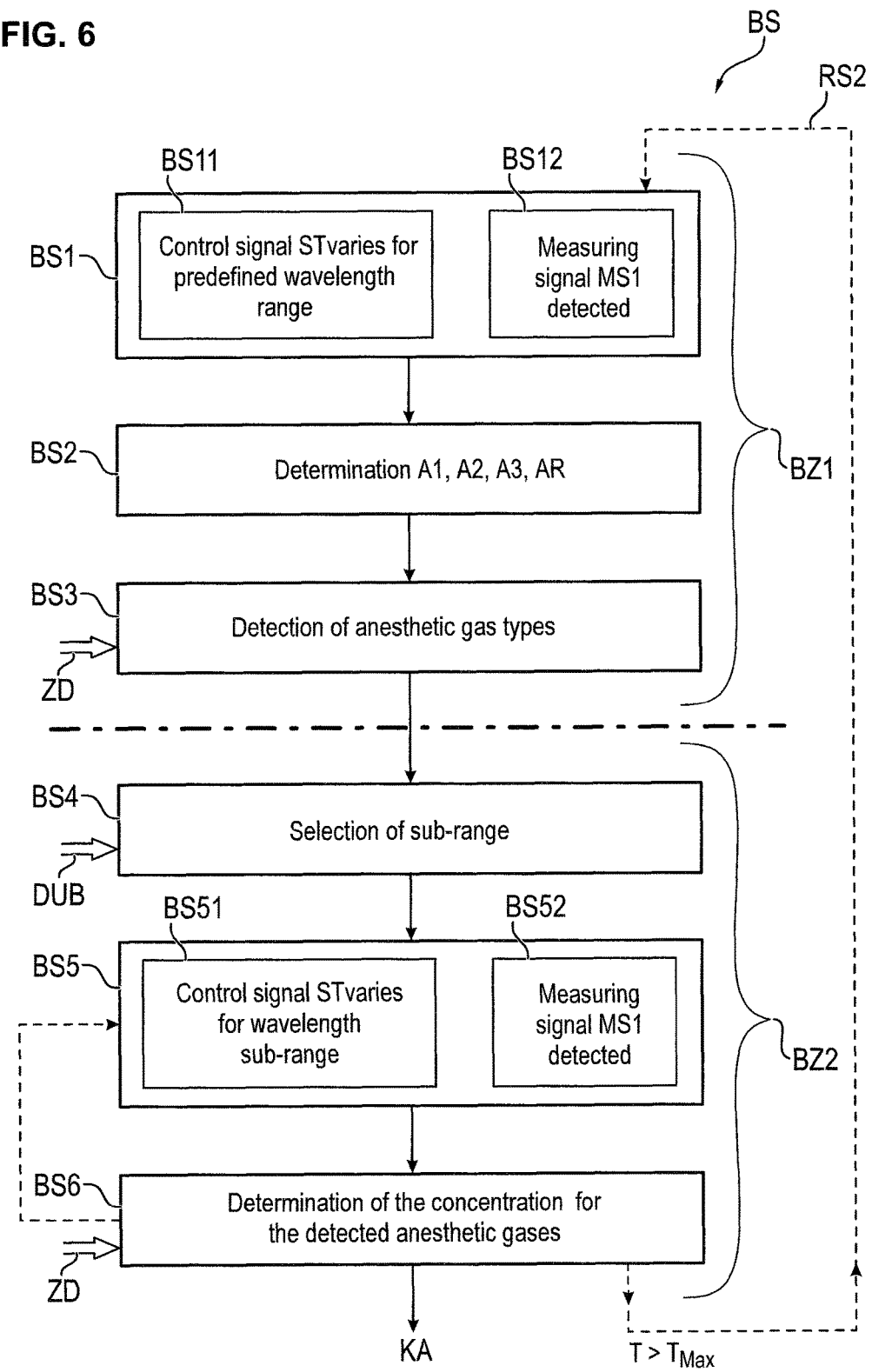
FIG. 6 is a flow diagram showing partial steps of a determination step according to the present invention.

FIG. 6 shows partial steps of the determination step BS from FIG. 4 in detail. Partial steps of the first operating mode BZ1 will be described at first.

Two substeps BS11 as well as BS12 are carried out simultaneously in a partial step BS1. In substep BS11, the computing and control unit activates the Fabry-Perot interferometer FPI1 by means of the control signal ST from FIG. 4 such that the central transmission wavelength of the band pass filter function scans over a predefined wavelength range. The computing and control unit correspondingly varies for this the control signal ST within the framework of step BS11. The control signal ST is preferably a control voltage, which will be discussed more specifically later.

In a substep BS12 running simultaneously, the computing and control unit R from FIG. 4 detects the measured signal MS1 of the first detector D1.

Different absorbance values A1, A2, A3 are determined at different measuring wavelengths as well as an absorbance value AR is determined at a reference wavelength in a partial step BS2.

Figure 1:
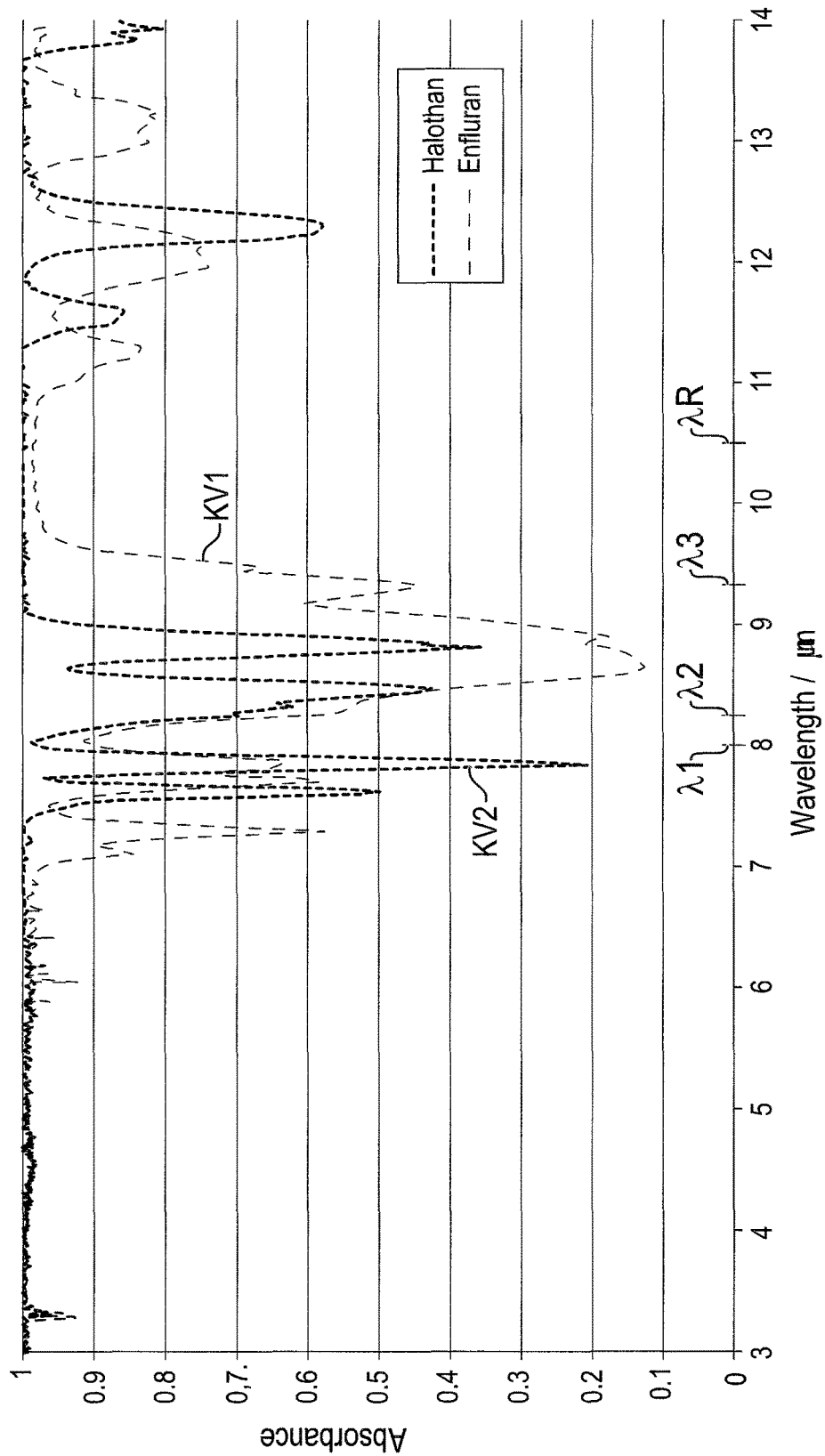
FIG. 1 is a diagram showing exemplary absorbance spectra for exemplary types of anesthetic gases.

If measurement is performed, for example, at a measuring wavelength $\lambda 1$, an intensity of the measured signal MS1 is detected as a reception intensity $IRX(\lambda 1)$ at a corresponding measurement time in the first operating mode. Further, if a transmission intensity $ITX(\lambda 1)$, which was sent at this wavelength $\lambda 1$ by the radiation source SQ according to FIG. 1, is known, absorbance A1 can be determined at this wavelength $\lambda 1$ according to $$A1 = \frac{IRX(\lambda 1)}{ITX(\lambda 1)}$$

A respective corresponding absorbance A2 or A3 can then be determined at further measurement times at additional measuring wavelengths $\lambda 2$, $\lambda 3$ according to $$A2 = \frac{IRX(\lambda 2)}{ITX(\lambda 2)}$$

$$A3 = \frac{IRX(\lambda 3)}{ITX(\lambda 3)}$$

The number M of measuring wavelengths equals M=3 with an index of m=1 . . . , M in this example.

Further, a corresponding absorbance AR can be determined at a reference wavelength $\lambda R$, for example, 10.5 µm, according to $$AR = \frac{IRX(\lambda R)}{ITX(\lambda R)}$$

The measuring wavelengths $\lambda 1$, $\lambda 2$, $\lambda 3$ may be selected here explicitly for the detection of a certain combination of types of anesthetic gases.

The manner in which the presence of respective types of anesthetic gases can be inferred in a partial step BS3 from FIG. 6 in case of a certain selection of the measuring wavelengths $\lambda 1$, $\lambda 2$, $\lambda 3$ will now be explained in detail.

The determination step BS3 uses for this a data set ZD, which indicates a relationship between different absorbance values A1, A2, A3, AR of different wavelengths $\lambda 1$, $\lambda 2$, $\lambda 3$, $\lambda R$ and a gas concentration of a type of anesthetic gas or to a plurality of gas concentrations of a plurality of types of anesthetic gases.

Figure 8:
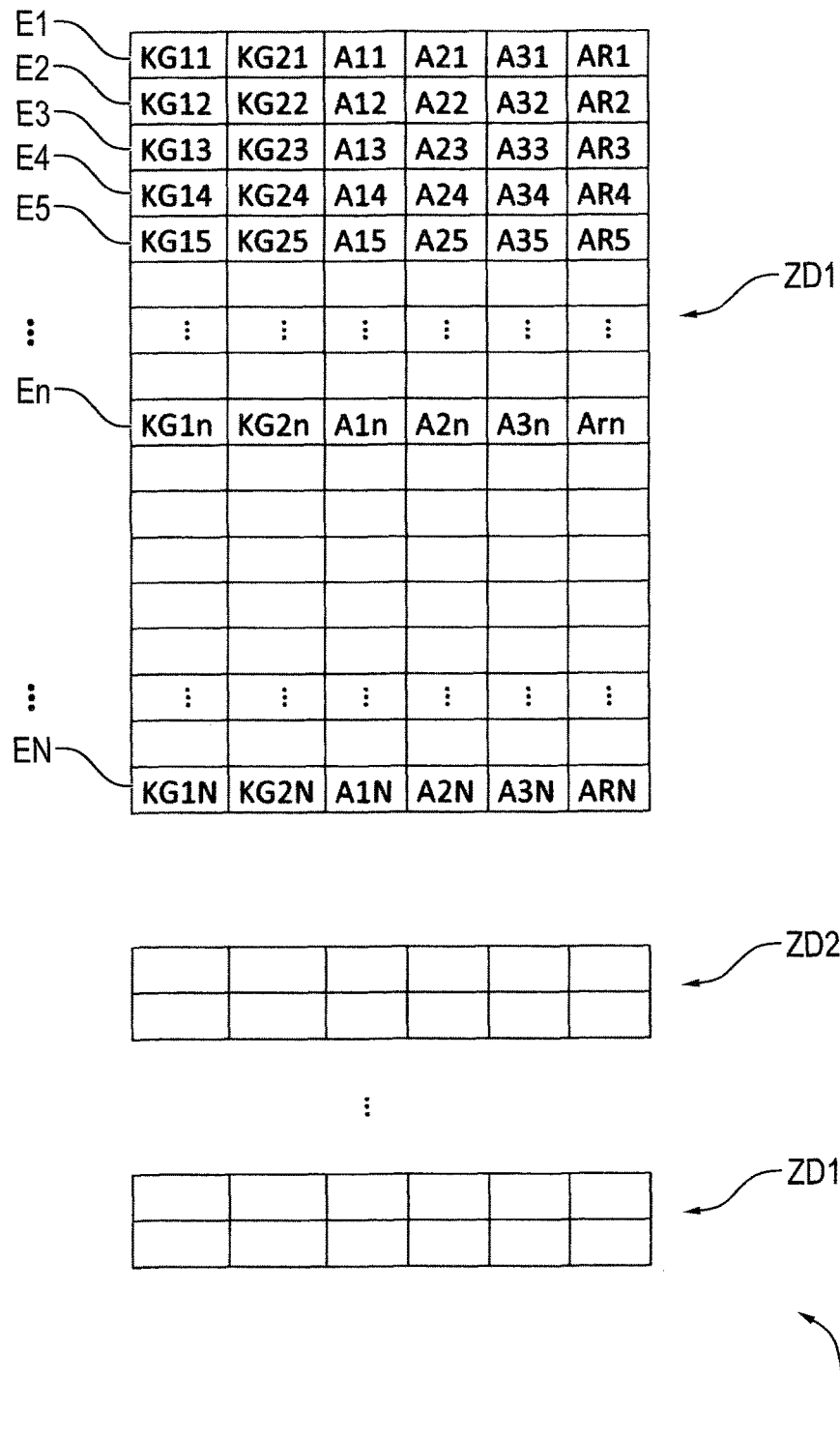
FIG. 8 is a diagram showing a data set for assigning absorbance values to concentration values.

FIG. 8 shows for this an exemplary assignment data set ZD, which has partial data sets ZD1, . . . , ZD10. Each of the partial data sets ZD1, . . . , ZD10 indicates respective combinations of measured concentrations of two types of anesthetic gases for respective combinations of absorbance values.

The partial data set ZD1 shall now be explained as a first example.

The partial data set ZD1 contains different entries E1 through EN with the respective index n=1 ..., N. For example, the entry E1 is to be defined here such that an assignment to certain absorbance values A11, A21, A31, AR1 of corresponding wavelengths λ1, λ2, λ3, λR is established for a certain concentration value KG11 of a first type of anesthetic gas and for a certain concentration value KG2 of a second type of anesthetic gas.

If, for example, the absorbance values A1, A2, A3, AR from the determination step BS2 in FIG. 6 are identical to the respective absorbance values A11, A21, A31, AR1 of the entry E1, it can then be inferred that a certain first type of anesthetic gas is present with a certain first concentration KG11 and a certain second type of anesthetic gas is present with a certain second concentration KG21 in the anesthesia ventilation gas or in the ventilation gas sample.

Further combinations of absorbance values at the different wavelengths λ1, λ2, λ3, λR are indicated for other combinations of concentration values KG11, ..., KG1N for the first type of anesthetic gas and of KG21, ..., KG2N for the second type of anesthetic gas.

In other words, if the measured absorbance values A1, A2, A3, AR are available, it is possible to determine on the basis of the data set ZD1 the particular entry E1, ..., EN that is most likely to correspond to these absorbance values A1, A2, A3, AR. This comparison can be achieved, for example, by finding a minimum of a mean distance indicator between the measured absorbance values A1, A2, A3, AR and certain absorbance values in the data set ZD1. Consequently, the entry with the index n for which a distance indicator $$Er(n) = \sum_{m=1}^{M} |(Amn - Am)|^2$$

is minimal is determined.

The assignment data set ZD1 can be regarded here as a representation of combinations of concentration values for a certain combination of certain types of anesthetic gases.

Corresponding entries can be stored in another data set ZD2 for another combination of another two certain types of anesthetic gas.

If, for example, five different types of anesthetic gas are to be detected, and it can be assumed that at most two types of anesthetic gas occur simultaneously, it would be sufficient for the assignment data set ZD to have ten partial data sets ZD1, ..., ZD10.

If only an individual type of anesthetic gas is present, the assignment data set ZD1 may also be used if there are entries for which the other type of anesthetic gas has a concentration with the value zero.

It was first explained how it can be checked on the basis of the measured absorbance values A1, A2, A3, AR which of the entries En of the data set ZD1 is most probable for the types of anesthetic gases being provided there.

Other respective most probable entries can be determined for other partial data sets ZD2, ..., ZD20 according to the type of the data set ZD1. A plurality of potential most probable entries can then be determined relative to the tables or partial data sets ZD1, ..., ZD20. Each of the potential most probable entries, which has the lowest distance indicator, is then selected as the one that provides information on which types of anesthetic gas are present and preferably at what concentrations they are present.

Figure 2:
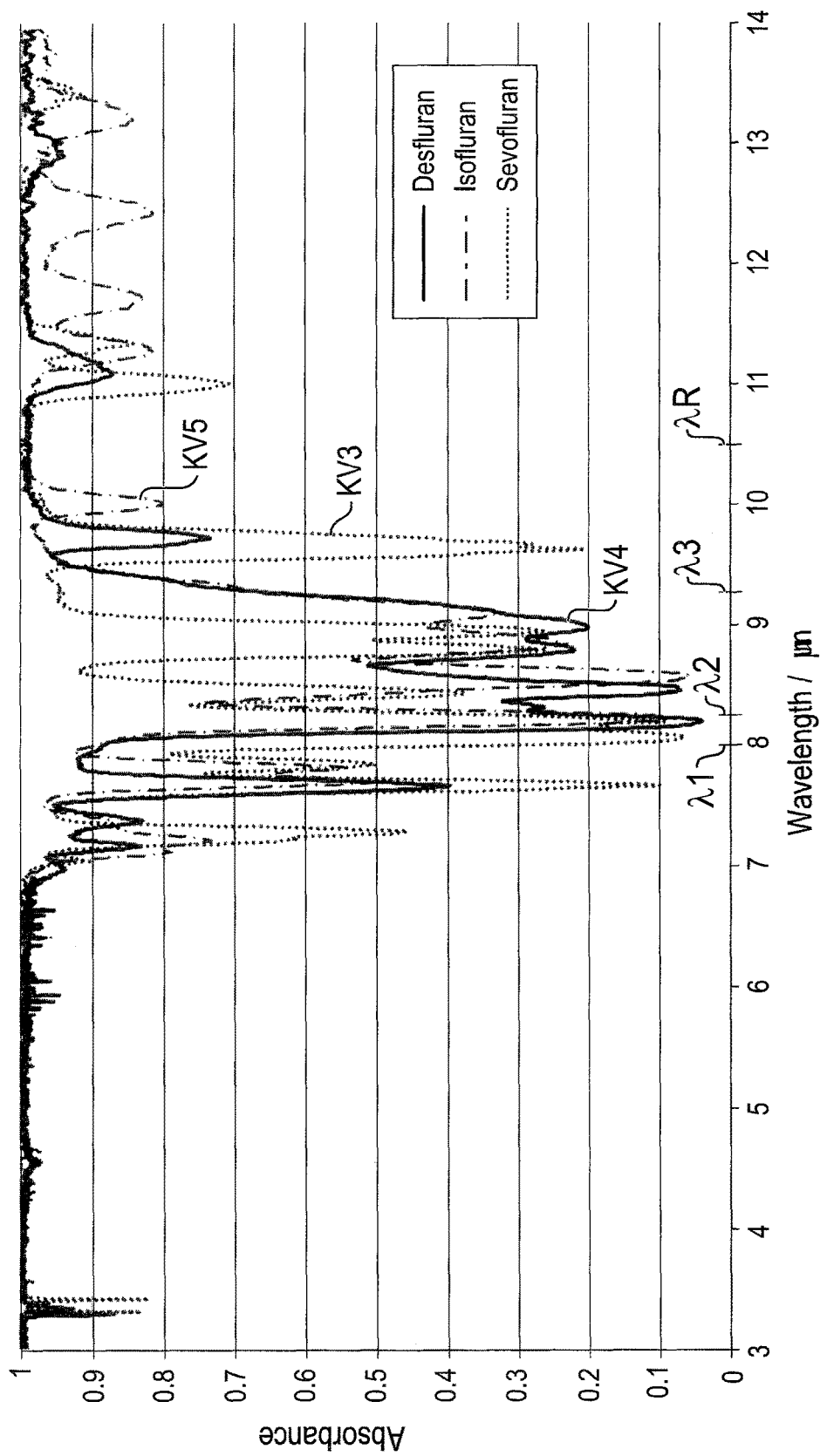
FIG. 2 is a diagram showing exemplary absorbance spectra for exemplary types of anesthetic gases.

It should be noted that different other measuring wavelengths λ1, λ2, λ3 may be necessary for different combinations of types of anesthetic gases, because, as was already explained before with reference to FIGS. 1 and 2, even though a certain measuring wavelength λ2 may, for example, be advantageous for a measurement relative to halothane and enflurane in FIG. 1, this wavelength may precisely be disadvantageous according to FIG. 2 for a measurement especially of desflurane. A respective partial data set ZD1, ..., ZD10 therefore represents an assignment of absorbance values, which must be measured at respective certain measuring wavelengths, to concentration values of types of anesthetic gases. The corresponding measuring wavelengths λ1, λ2, λ3 may consequently be individual or different for each partial data set ZD1, ..., ZD10.

If the most probable entry is such for which one of the two concentrations for a certain type of anesthetic gas is exactly zero, it can be assumed that this type of anesthetic gas is not present, or else that it is precisely the particular type of anesthetic gas that is also represented by this entry of the corresponding partial data set.

In summary, it can consequently be stated that a respective presence in the ventilation gas sample can be detected on the basis of the absorbance values A1, A2, A3, AR by means of the assignment data set ZD for respective, potential types of anesthetic gases. Which particular potential type of anesthetic gas is present in the ventilation gas sample GP is consequently detected on the basis of the measured signal MS1 or MSD1 from FIG. 4.

As was noted above, different other measuring wavelengths λ1, λ2, λ3 may be necessary for different combinations of types of anesthetic gases. Consequently, a relatively broad, predefined wavelength range with greatly different measuring wavelengths must therefore be swept in order to perform a detection of respective potential types of anesthetic gases with respect to their respective presence with certainty.

The detection of the presence of types of anesthetic gases, which was explained in reference to FIG. 8 and which is to be performed in the determination step BS3, can consequently be carried out on the basis of the assignment data set ZD.

The determination of the concentration values proper for the detected types of anesthetic gases, as it was likewise explained already with reference to FIG. 8, does not necessarily have to be carried out in step BS3 of FIG. 6.

Returning to FIG. 6, the partial steps of the second operating mode BZ2 will now be explained in more detail.

Depending on the types of anesthetic gases detected as being present, a subrange of the predefined wavelength range is selected in a partial step BS4.

This is preferably performed on the basis of a data set DUB, which is shown in FIG. 9. The data set DUB indicates respective subranges of the predefined wavelength range for respective combinations of types of anesthetic gases.

The data set DUB indicates respective subranges (UBk) with the index k=1 ... K, which are each suitable for a concentration measurement of the respective types of anesthetic gases in the second operating mode, for respective tuples of types of anesthetic gases {Gi} with the index I. A subrange, presented here by an entry {UBk}, may be specified, for example, by an upper critical wavelength and a lower critical wavelength.

Instead of the respective subranges {UBk}, it is also possible to specify respective tuples of preferred wavelengths within such a subrange, which are then to be used as the measuring wavelengths for the concentration measurement in the second operating mode. If only a single type of anesthetic gas was detected, it is also possible that such an entry consists of only an individual preferred wavelength.

Consequently, if the central transmission wavelength of the band pass filter function was varied at first, for example, from 7 μm to 11 μm in the first operating mode in order to enable the detection of all potential types of anesthetic gases, a subsequent concentration measurement can be performed with fixed measuring wavelengths λ1, λ2, λ3 in the second operating mode after the result of this detection is available. An absorbance indicator at the wavelength λR can continue to be used here from the first operating mode, because such an absorbance at the reference wavelength λR is only subject to a slow change over time due to the effects to be detected or to be compensated.

The advantage is consequently that it is no longer necessary to scan the full predefined wavelength range from the first operating mode in the second operating mode for an accurate concentration measurement of the detected types of anesthetic gases, but it is possible to use one or more preferred wavelengths of a subrange of the predefined wavelength range. As a result, a shorter duration is necessary now for an individual measurement for the determination of the concentration in the second operating mode than the minimum duration for scanning the entire predefined wavelength range in the first operating mode.

The partial step BS5 shows for this the simultaneous performance of two substeps BS51 as well as BS52.

The control signal ST is varied by the computing unit in the substep BS51 such that the central transmission wavelength is only varied in the subrange. At the same time, the measured signal MS1 or MSD1 of the detector D1 is detected in a substep BS52.

Respective gas concentration values for the respective types of anesthetic gases, which were detected before, are then determined in a subsequent partial step BS6 for different consecutive times.

Such a determination of the concentration values for the respective types of anesthetic gases may be carried out on the basis of absorbance values as well as of an assignment data set, as it was explained above in connection with the assignment data set ZD from FIG. 8.

The exact performance of the wavelength variation in the first operating mode BZ1 and in the second operating mode BZ2 for measuring a plurality of concentration values for a detected type of anesthetic gas or for a plurality of detected types of anesthetic gases at the consecutive times will be explained in more detail later with reference to FIGS. 11 through 14.

A set or a data set KA, which has a plurality of respective concentration values for consecutive times for respective types of anesthetic gases detected as being present is finally provided. The second operating mode BZ2 can be continued continually in such a way that the steps BS5 and BS6 can be repeated in their sequence multiple times in order also to determine additional concentration values at additional times.

There preferably is a changeover from the second operating mode BZ2 back to the first operating mode BZ1 after the end of a predefined maximum time period Tmax.

Figure 11:
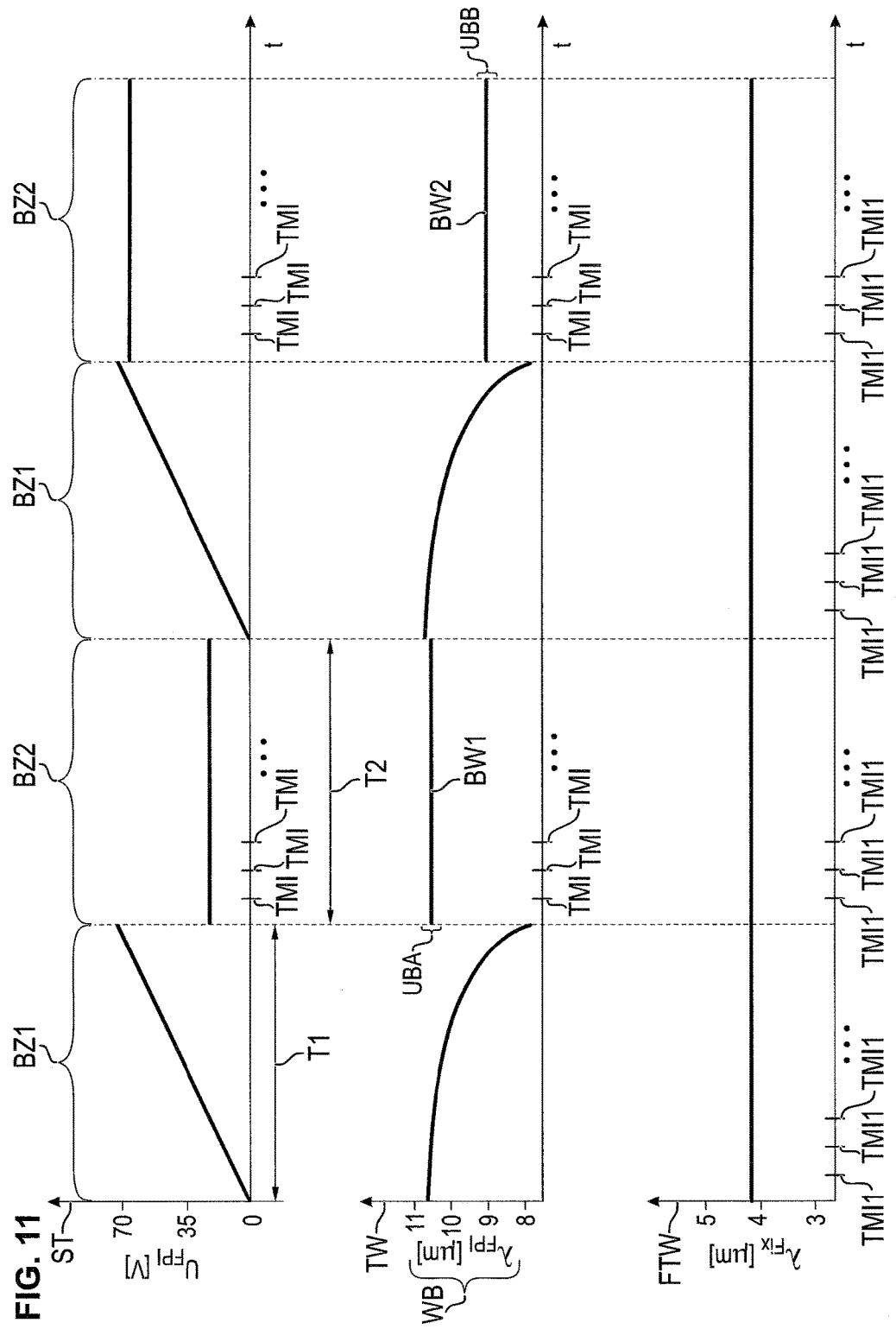
FIG. 11 is a diagram showing possible curves of a control signal as well as of a wavelength range according to a first variant.

FIG. 11 shows a first variant for the selection of a subrange during the second operating mode as a function of an individual anesthetic gas type. Shown is a curve of the control signal ST, which is preferably a control voltage, during the first operating mode BZ1 as well as during the second operating mode BZ2.

The first operating mode BZ1 has a duration T1. The second operating mode BZ2 has a duration T2, which may be equal to the first duration T1 of the first operating mode, or it may be longer.

The control signal ST is selected during the first operating mode BZ1 to be such that the central transmission wavelength TW scans over a predefined wavelength range WB of preferably 8 μm to 10.6 μm.

As was mentioned before, it is necessary to scan over such a broader, predefined wavelength range, because greatly different types of anesthetic gases must be detected during the first operating mode.

If only an individual type of anesthetic gas was detected in the first operating mode BZ1, one measurement is sufficient for the determination of the concentration values in the second operating mode BZ2 at an individual wavelength. The central transmission wavelength TW is consequently selected by the computing and control unit by means of the control signal ST such that the central transmission wavelength TW corresponds to the preferred wavelength BW1 being shown here. Consequently, a very narrow-band subrange UBA of the predefined wavelength range WB is thus selected.

A plurality of concentration values can then consequently be determined at consecutive times TMI for the one type of anesthetic gas detected as being present on the basis of the measured signal of the detector in the second operating mode BZ2. Since the detection result at the reference wavelength from the first operating mode BZ1 is taken into account, the central transmission wavelength TW does not have to be varied any further, but it can be maintained at a constant value, which makes possible a high temporal resolution with measurement times TMI located close to one another during the second operating mode BZ2. Furthermore, if a concentration measurement were performed by means of a complete scan over the predefined wavelength as in the first operating mode BZ1, measurement times would be obtained that would be spaced markedly farther apart than the measurement times TMI in the second operating mode BZ2.

In other words, a concentration measurement of a type of anesthetic gas or of a plurality of types of anesthetic gases is possible in the first operating mode BZ1 with a first temporal resolution, whereas a concentration measurement of a type of anesthetic gas is possible in the second operating mode BZ2 with a second temporal resolution, the second temporal resolution being higher than the first temporal resolution.

If this second operating mode BZ2 is followed, in turn, by the first operating mode BZ1, in which the central transmission wavelength scans again the predefined wavelength range WB by means of the control signal ST, and if the detection result in the first operating mode is, further, such that an individual but other type of anesthetic gas was detected, the Fabry-Perot interferometer FPI can then be actuated in yet another subsequent second operating mode BZ2 by means of the control signal ST such that the central transmission will assume a different, preferred wavelength BW2. Consequently, a relatively narrow-band subrange UBB of the predefined wavelength range WB is then selected.

Figure 12:
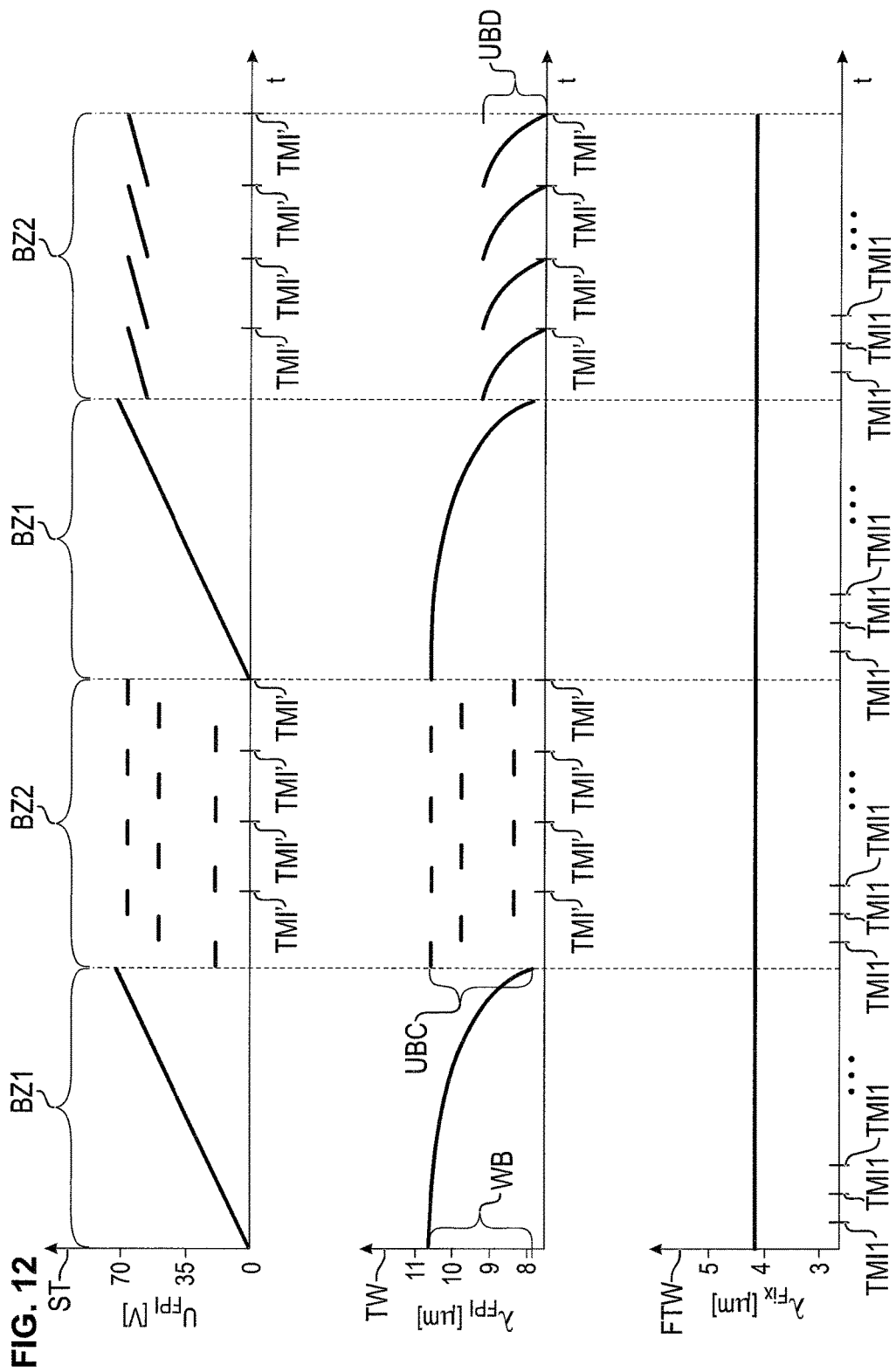
FIG. 12 is a diagram showing possible curves of the control signal and of the central transmission wavelength according to a second variant.

FIG. 12 shows possible curves of the control signal ST as well as of the central transmission wavelength TW over time for a second variant. More than one type of anesthetic gas is detected in the first operating mode BZ1 in this second variant. It is therefore necessary that more than one measuring wavelength be actuated in the second operating mode BZ2 in order to make possible a concentration measurement for the plurality of types of anesthetic gases.

If, for example, two defined types of anesthetic gases were detected in the first time window during the first operating mode BZ1, the control signal ST can be selected in the second operating mode BZ2 such that certain control signal steps are approached in steps, so that the central transmission wavelength TW scans certain preferred measuring wavelengths, which are located in a subrange UBC. As was explained above, at least three measuring wavelengths must be used for a measurement of two respective concentration values of respective types of anesthetic gases. Consequently, if the three preferred measuring wavelengths were scanned, a determination of concentration values can then be performed at a measuring time TMI' for the two types of anesthetic gases. If the preferred measuring wavelengths are scanned one more time, new concentration values can then be transmitted for the two types of anesthetic gases. As a result, corresponding measurement times TMI' are obtained, at which respective concentration values can be determined for the respective types of anesthetic gases detected as being present. Consequently, the determination of a plurality of concentration values is performed at times TMI' following one another for each detected type of anesthetic gas during the operating mode BZ2.

Even though the temporal resolution of the measurement times TMI' is lower in this second variant of the concentration value measurement from FIG. 12 than for the measurement times TMI in FIG. 11 in case of only one anesthetic gas type, the temporal resolution of the measurement times TMI' is nevertheless higher than if a measurement were always performed on the basis of a complete scanning of the complete wavelength range for determining a concentration value of a type of anesthetic gas or for determining two concentration values of respective anesthetic types, as it is provided by the first operating mode BZ1.

In other words, a concentration measurement of a type of anesthetic gas or of a plurality of types of anesthetic gases is possible with a first temporal resolution in the first operating mode BZ1, whereas a concentration measurement of a type of anesthetic gas or of a plurality of types of anesthetic gases is possible with a second temporal resolution in the second operating mode BZ2, the second temporal resolution being higher than the first temporal resolution.

In a fourth time window, FIG. 12 shows another variant for varying the central transmission wavelength in a selected subrange UBD. The control signal ST is varied here continuously, so that the preferred wavelength is also varied continuously within the subrange UBD. Corresponding measuring times TMI' with a certain temporal resolution, which is higher than a temporal resolution in case of a concentration measurement that can be performed in the first operating mode BZ1, are obtained here as well.

In the sense of this application, a succession of times does not have to be a direct succession of times, because a succession occurring in such a way that even though these times are not directly adjacent in time but are located one after another time is sufficient.

It is consequently possible to actually focus in the second operating mode BZ2 on the wavelengths that are adjusted for a measurement of such types of anesthetic gases whose presence was detected in the first operating mode BZ1.

As is seen from FIG. 11 and FIG. 12, the central transmission wavelength TW scans over at least one partial range from 8 µm to 9 µm in the first operating mode.

The preferred wavelengths BW1, BW2 are preferably selected such that the types of anesthetic gases detected as being present will have a predefined minimum of an energy absorption at these wavelengths. It is ensured hereby that the adoption measurements are performed at wavelengths at which a sufficient measuring accuracy is to be expected based on the minimum of the energy absorption.

According to FIG. 4, the device AV1 according to the present invention further has in this preferred embodiment a fixed optical filter FOF, which has a fixed central transmission wavelength between 4 µm and 5 µm.

Another detector D100, which is preferably present, is likewise arranged at the end of the measuring path. The detector D100 provides an additional measured signal MS100, which indicates a second intensity S2 of the infrared radiation S, which intensity was transmitted through the fixed band pass filter function of the fixed optical FOF. The additional measured signal MS100 may be considered to be a second measured signal.

By means of the A/D converter AD, the computing unit R converts the second measured signal MS100 into a digital second measured signal MSD100, which corresponds to the second measured signal MS100.

The computing unit R determines a plurality of concentration values KC at a plurality of consecutive times for carbon dioxide on the basis of the second measured signal MS100 or MSD100 at least in the second operating mode.

FIGS. 11 and 12 show for this the fixed transmission wavelength FTW of the fixed optical filter FOF from FIG. 4. A concentration determination for carbon dioxide is possible now at corresponding measurement times TMI1 at least during the second operating mode BZ2, but preferably also during the first operating mode BZ1.

As a result, a determination of concentration values for carbon dioxide can consequently be carried out simultaneously to the determination of concentration values for types of anesthetic gases, analogously to the determination of concentration values for types of anesthetic gases.

Figure 5:
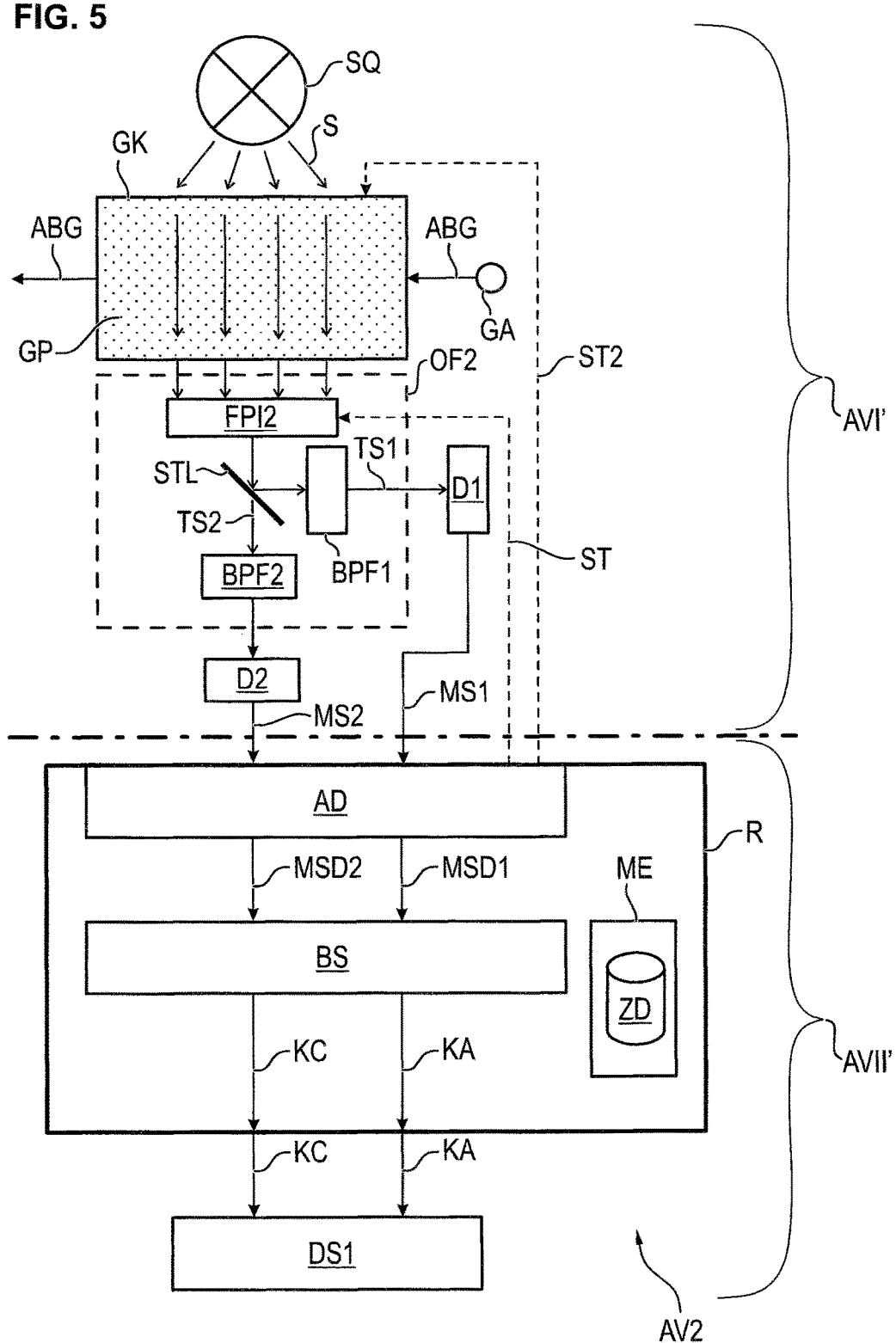
FIG. 5 is a schematic view of another preferred embodiment of the device according to the present invention.

FIG. 5 shows another preferred embodiment AV2 of the device being proposed for the analysis of an anesthesia ventilation gas.

The device AV2 can be divided into a first partial device AVI' and a second partial device AVII'.

According to this embodiment, the device AV2 has a Fabry-Perot interferometer FPI2 instead of the Fabry-Perot interferometer FPI1 from FIG. 4.

This Fabry-Perot interferometer FPI2 has a plurality of band pass filter functions of different orders. The above-mentioned band pass filter function is a first band pass filter function of a first-type order here with a first central transmission wavelength and an additional band pass filter function of a second-type order with a second central transmission wavelength. FIG. 7 shows as an example for this the second band pass filter function BP2 with a corresponding second central transmission wavelength TW2. The first band pass filter function BP1 has a first central transmission wavelength TW1 in this case.

The first-type order is consequently the second order and the second-type order is consequently the fifth order in this exemplary embodiment.

Figure 15:
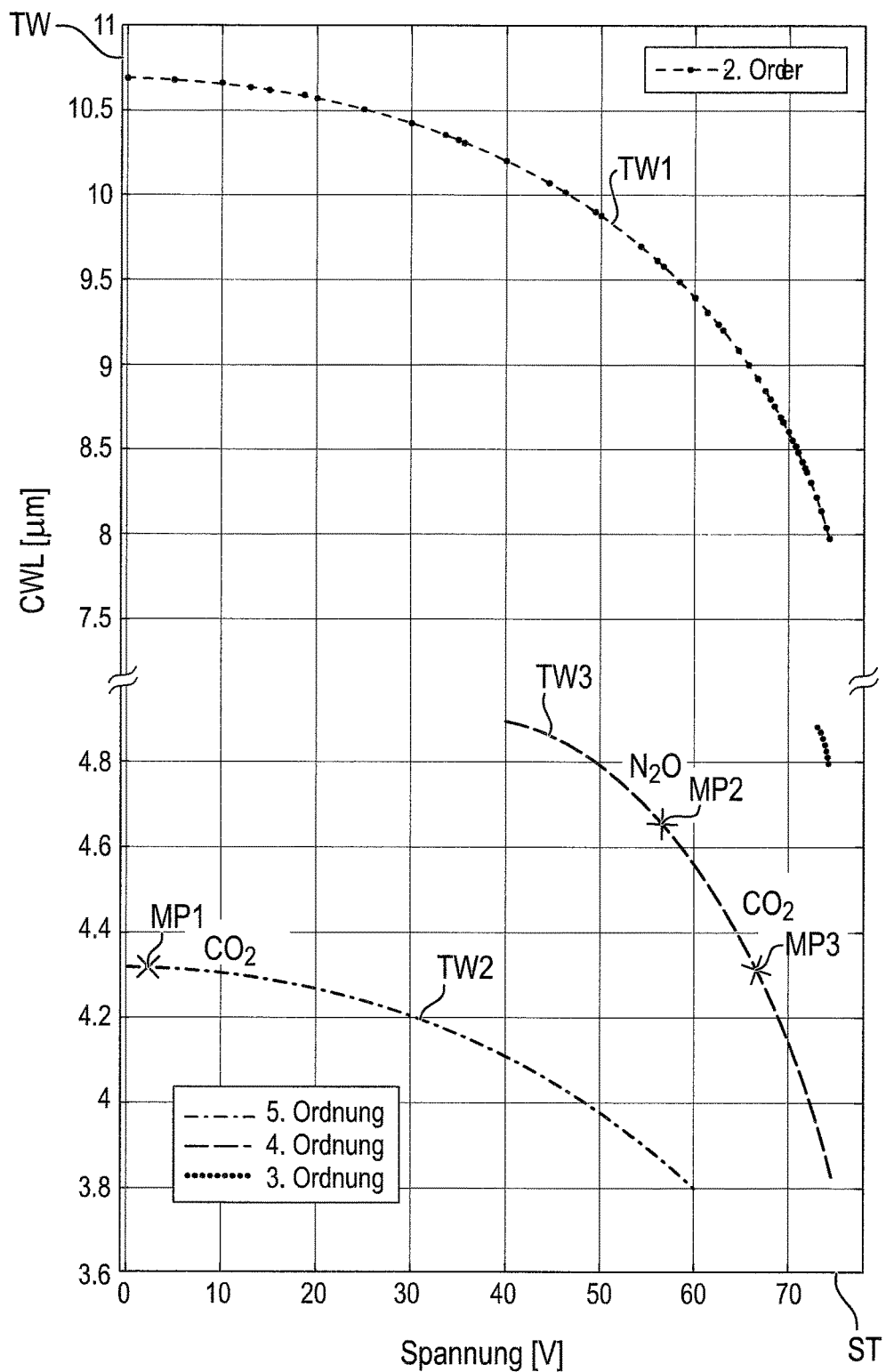
FIG. 15 is a flow diagram showing a variation of different central transmission wavelengths of different orders of a Fabry-Perot interferometer.

FIG. 15 shows as an example for this a different transmission wavelength TW for different orders as a function of the control signal ST. Four different orders, second order through fifth order, are shown in this example shown in FIG. 15.

The Fabry-Perot interferometer FPI2 in FIG. 5 preferably has as the first band pass filter function a band pass filter function with a central transmission wavelength with the first-type order as the second order.

Further, the additional, second band pass filter function with the second central transmission wavelength is of such a type that this corresponds to the second-type order as the fifth order.

The first detector D1 mentioned from FIG. 4 is complemented according to the exemplary embodiment from FIG. 5 by an additional, second detector D2, which is configured to provide an additional measured signal MS2, which can be considered to be a second measured signal MS2. The additional or second measured signal MS2 indicates a second intensity S2 of the infrared radiation S2, which intensity was transmitted through the gas cuvette GK and through the second band pass filter function of the Fabry-Perot interferometer FPI2. To filter the second band pass filter function BP2 of the Fabry-Perot interferometer, a fixed optical band pass filter BPF2, whose fixed band pass filter function BPFF2 is shown in FIG. 7, is located between the radiation source SQ and the second detector D2. The second intensity S2 is precisely also an intensity that was transmitted through the gas cuvette GK, the second band pass filter function of the Fabry-Perot interferometer FPI2 and the second fixed optical band pass filter BPF2 to the second detector D2.

This is preferably achieved by the infrared radiation passing through the Fabry-Perot interferometer FPI2 being split by means of a beam splitter STL into two intensities or infrared radiation components TS1 and TS2 in a wavelength-dependent manner. A first radiation component TS1 above preferably 6 µm falls on the first detector D1 and a second component below preferably 6 µm falls on the second detector D2.

The device AV2 consequently has an optical partial device OF2. This optical partial device OF2 has the Fabry-Perot interferometer FPI2 as well as the two fixed band pass filters BPF1, BPF2. The optical partial device OF2 preferably has the beam splitter STL. The optical partial device OF2 is configured to select the first intensity S1 of the infrared radiation and to guide it onto the first detector D1. Further, the optical partial device OF2 is configured to select the second intensity S2 of the infrared radiation and to guide it onto the second detector D2.

The computing and control unit R converts the measured signals MS1, MS2 into corresponding digital measured signals MSD1 and MSD2, respectively, by means of the analog/digital converter AD.

The above-described determination of the concentration values KA for the types of anesthetic gases on the basis of the first measured signal MSD1 as well as the determination of concentration values KC for carbon dioxide on the basis of the second measured signal MSD2 are then performed in the determination step BS.

The computing unit R now actuates the Fabry-Perot interferometer FPI2 by means of the control signal ST such that the second central transmission wavelength of the second band pass filter function BP2 from FIG. 7 corresponds, at least at times, to an additional preferred wavelength between 4 µm and 5 µm.

Figure 13:
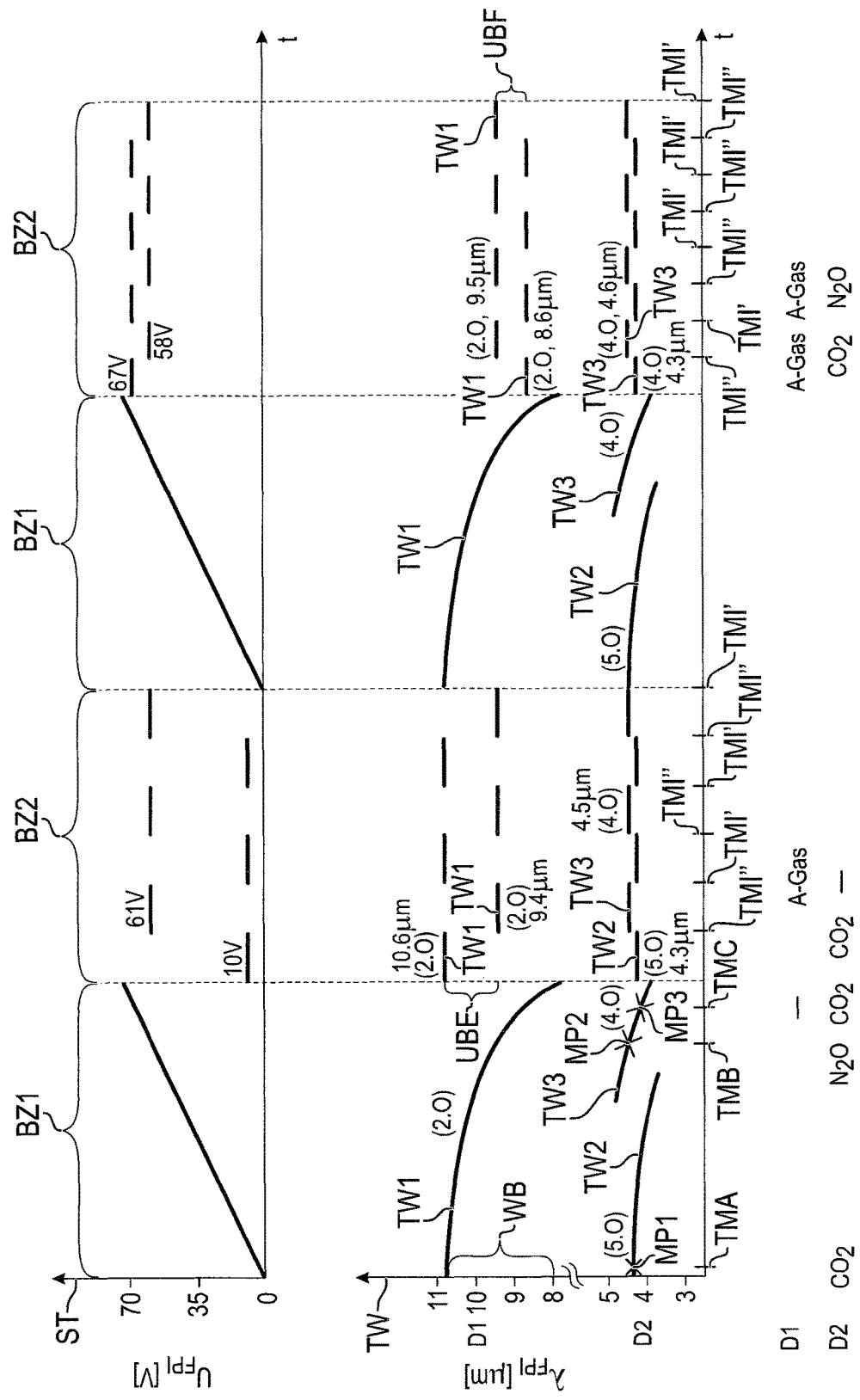
FIG. 13 is a diagram showing curves of the control signal as well as a plurality of central transmission wavelengths according to a third variant.
Figure 14:
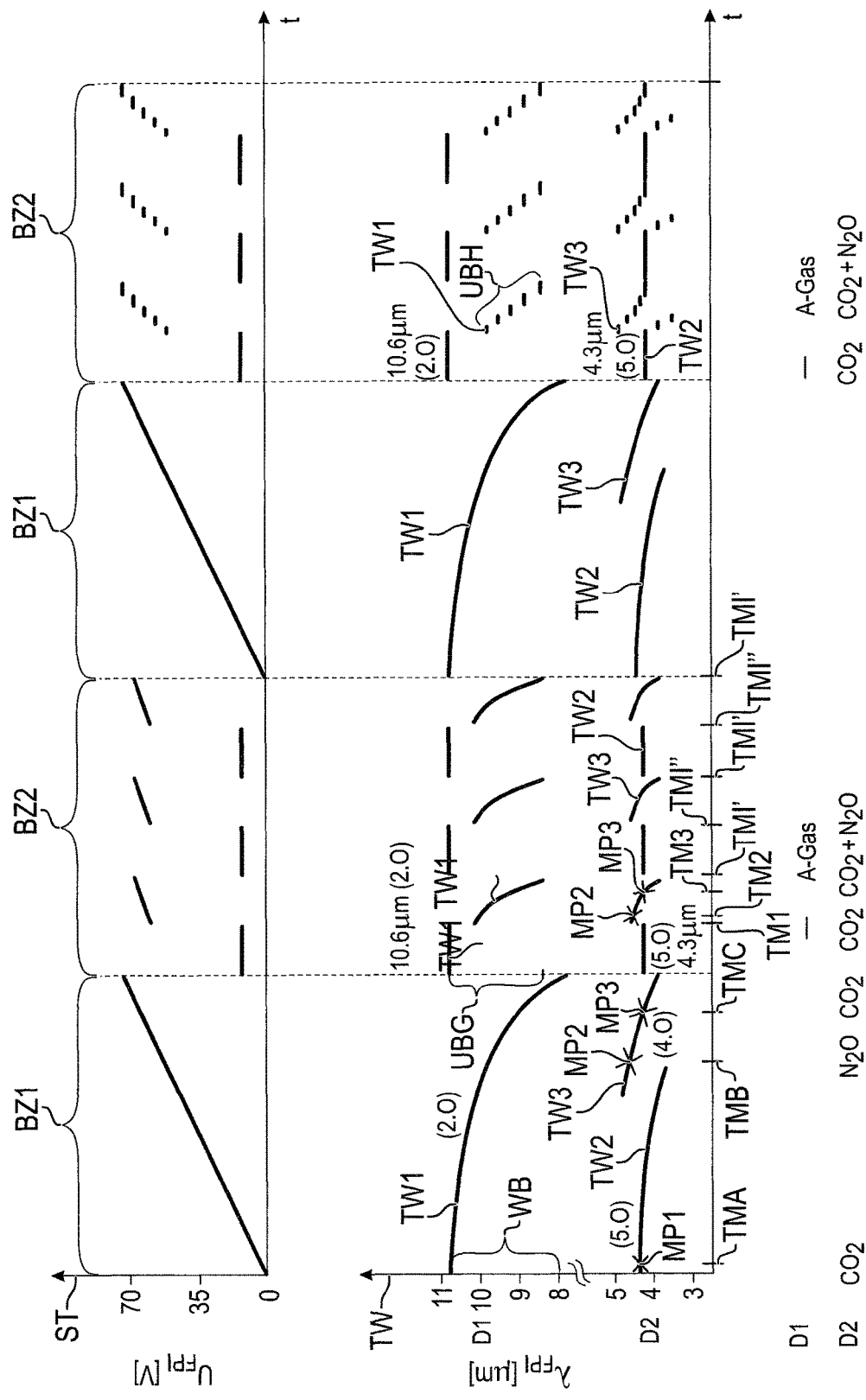
FIG. 14 is a flow diagram showing possible curves of the control signal as well as of the plurality of central transmission wavelengths according to a fourth variant.

FIGS. 13 and 14 show for this different variants of a selection of the central transmission wavelength TW1 and TW2 for the different band pass filter functions of the different orders of the Fabry-Perot interferometer. FIGS. 13 and 14 further show another central transmission wavelength TW3 of another band pass filter function BP3 of the Fabry-Perot interferometer, which can be assigned according to FIG. 7 to another order, here to the fifth order, because it is possible that, as is seen in FIG. 15, the control signal ST is changed into a range, preferably, for example, 65 V, so that the central transmission wavelength TW3 of the band pass filter function BP3 may assume values that coincide with possible values of the central transmission wavelength TW2 of the band pass filter function BP2 for other values of the control signal ST, preferably, for example, 2 V.

According to FIG. 13, a variation or a scan of the predefined wavelength range WB is again performed by the central transmission wavelength TW1 in the first operating mode BZ1 based on the control signal ST. The first intensity S1 of the infrared radiation, which intensity was transmitted through the first band pass filter function of the Fabry-Perot interferometer, then consequently falls on the first detector D1 from FIG. 5.

At the same time, a change or a variation of the transmission wavelength TW2 of the additional, second band pass filter function BP2 from FIG. 7 occurs as viewed by the second detector D2.

The second intensity S2 of the infrared radiation, which passes through the second band pass filter function of the Fabry-Perot interferometer, then consequently reaches the detector D2 shown in FIG. 5.

Figure 3:
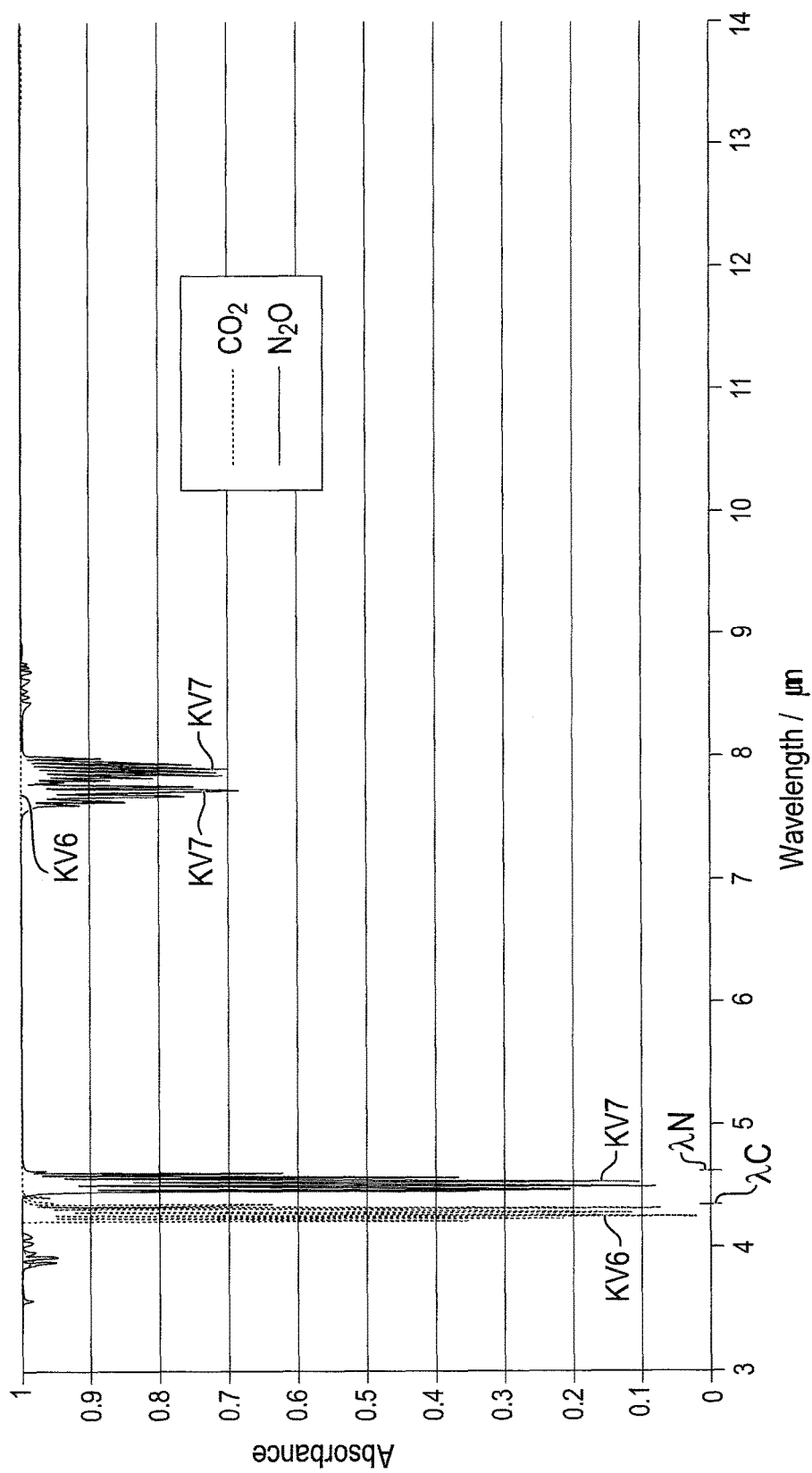
FIG. 3 is a diagram showing absorbance curves for carbon dioxide and dinitrogen monoxide.

As is seen in FIG. 3 based on the absorbance curve K6 for carbon dioxide with the measuring wavelength $\lambda C$, an absorbance measurement can then consequently be performed for carbon dioxide at a time TMA or measurement point MP1 with a wavelength of 4.3 µm at the second detector D2. This measurement point MP1 is likewise shown in FIG. 15 for the central transmission wavelength TW1 of the second order.

The third central transmission wavelength TW3 can preferably be used to perform an absorbance measurement for dinitrogen monoxide at an additional time TMB or measurement point MP2 at a wavelength of 4.62 µm, as can be seen in FIG. 3 on the basis of the absorbance curve K7 for dinitrogen monoxide with the measuring wavelength $\lambda N$. This measurement point MP2 is also shown in FIG. 15. This measurement is carried out by means of the detector D2 shown in FIG. 5.

Further, another measurement for carbon dioxide can be performed at a wavelength of 4.3 µm at an additional measurement point MP3 or time TMC based on the third central transmission wavelength TW3 of the third band pass filter function BP3. This measurement point MP3 is also shown in FIG. 15. This measurement is likewise carried out by means of the detector D2 shown in FIG. 5.

The first central transmission wavelength TW1 is then limited to a subrange UBE during the second operating mode BZ2 for measuring concentration values of an anesthetic gas type.

It is possible now, for example, to focus only on a measurement at a wavelength of 9.4 µm, because, for example, the additional wavelength of 10.6 µm could be unsuitable per se for measuring a detected type of anesthetic gas with respect to absorbance.

Consequently, possible consecutive times TMI' arise for the concentration measurement for a measurement of concentration values of the detected anesthetic gas type.

Based on the second measured signal MS2 or MSD2 from FIG. 5, central transmission wavelengths TW2, as shown in FIG. 13, can then be detected at the second detector D2 in the second operating mode BZ2 in order to determine concentration values for carbon dioxide at consecutive times TMI".

Consequently a plurality of concentration values are determined at consecutive times TMI" by means of the detector D2 or on the basis of the second measured signal MS2 or MSD2 for carbon dioxide during the second operating mode. Here as well, the temporal resolution of the measurement points TMI" is greater in the second operating mode than the value that could be obtained in the first operating mode BZ1.

In summary, it can be noted that due to a variation of the second transmission wavelength TW2 at least at times, this wavelength TW2 corresponds to a preferred wavelength between 4 μm and 5 μm.

The second operating mode BZ2 is again followed by the first operating mode BZ1, in which possibly present types of anesthetic gases are detected on the basis of the first measured signal MS1 from FIG. 5 in the above-described manner.

In yet another subsequent second operating mode BZ2, the central transmission wavelength TW1 is then limited to a subrange UBF of the predefined wavelength range WB. Absorbance measurements can now preferably be performed at times TMI' as well as TMII' for an individual anesthetic gas at both the wavelength of 8.6 μm and the wavelength of 9.5 μm. This is carried out by means of the measured signal detector D1 from FIG. 5.

The wavelengths of 4.3 μm of the third transmission wavelength TW3, which are obtained simultaneously, can likewise be used. A determination of concentration values for carbon dioxide is then performed on the basis of the second measured signal MS2 or MSD2. This is carried out at the times TMI".

It is, however, also possible to use the wavelength of 4.6 μm of the third transmission wavelength TW3, which is obtained simultaneously. A determination of concentration values for dinitrogen monoxide is then performed on the basis of the second measured signal MS2 or MSD2, This is carried out at the times TMI'.

In other words, a concentration measurement of a type of anesthetic gas or of a plurality of types of anesthetic gases is possible with a first temporal resolution in the first operating mode BZ1, whereas a concentration measurement of a type of anesthetic gas is possible with a second temporal resolution in the second operating mode BZ2, the second temporal resolution being higher than the first temporal resolution.

FIG. 14 shows curves of the control signal ST as well as of the transmission wavelength TW1 for such a variant, in which a plurality of types of anesthetic gases are detected in the first operating mode BZ1. A measurement is performed in the first operating mode BZ1 for carbon dioxide as well as dinitrogen monoxide in the first operating mode BZ1, as was already explained above with reference to FIG. 13.

A determination of concentration values for two different anesthetic gases is performed in the second operating mode BZ2.

The first central transmission wavelength TW1 is limited to a subrange UBG within the wavelength range WB in the second operating mode BZ2. No anesthetic gas measurement is performed during a wavelength of 10.6 μm, which is obtained first. If the first central transmission wavelength TW1 scans over a range of about 8 μm to 10 μm, an anesthetic gas measurement is then preferably performed here for two types of anesthetic gases at times TMI'.

Further, a carbon dioxide concentration is measured at times TM1 as well as TMI" by means of the second measured signal at the second detector by means of the second transmission wavelength TW2 at a wavelength of 4.3 μm. Consequently, a determination of concentration values for carbon dioxide is performed at a plurality of consecutive times by means of the second measured signal.

A measurement of a carbon dioxide concentration is likewise possible by means of the third transmission wavelength TW3 at a time TM3 or measurement point MP3.

Further, a concentration measurement for dinitrogen monoxide can be performed by means of the third transmission wavelength TW3 at a time TM2 or measurement point MP2.

The measurement points MP1, MP2, MP3 are also shown in FIG. 15.

While a continuous variation of the central transmission wavelengths TW1 as well as TW3 can take place according to FIG. 14 in this second operating mode BZ2, it is thus possible that these transmission wavelengths are varied step by step, instead in the second operating mode BZ2 in the far right part in the diagram shown in FIG. 14.

Figure 10A:
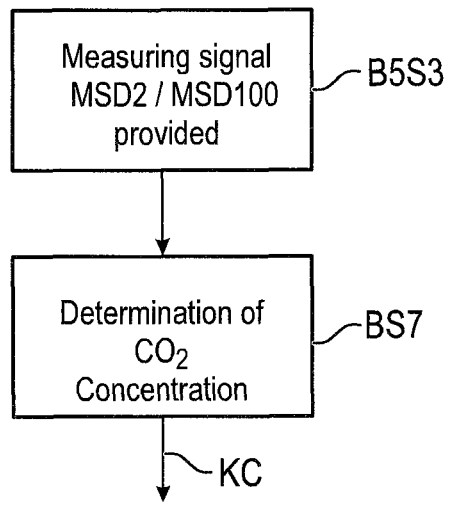
FIG. 10a is a flow diagram showing optional steps for a carbon dioxide concentration determination.
Figure 10B:
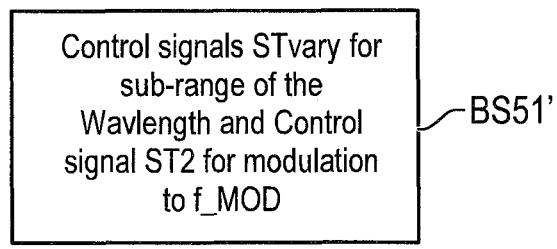
FIG. 10b is a diagram showing an optional partial step in connection with an amplitude modulation of the infrared radiation source.

FIG. 10a shows optional steps as parts of step BS5 from FIG. 6 for the determination of the concentration values for carbon dioxide.

Instead of the partial step BS51, detection of the measured signal MSD100 or of the measured signal MSD2 as the second measured signal takes place in an optional partial step BS53. If the embodiment is the embodiment AV1 of the device proposed in FIG. 4, the signal MS100 or MSD100 is detected as the second measured signal. If the embodiment is the embodiment AV2 of the device proposed in FIG. 5, the signal MS2 or MSD2 is detected as the second measured signal. For the determination of the carbon dioxide concentrations, the computing unit R from FIG. 4 or 5 performs, simultaneously to the partial step BS6 in FIG. 6, a partial step BS7, in which the determination of the carbon dioxide concentration values is performed on the basis of the second measured signal MS2 or MSD2 or MS100 or MSD100.

In other words, a concentration measurement of a type of anesthetic gas or of a plurality of types of anesthetic gases is possible in the first operating mode BZ1 with a first temporal resolution, whereas a concentration measurement of a type of anesthetic gas or of a plurality of types of anesthetic gases is possible in the second operating mode BZ2 with a second temporal resolution, the second temporal resolution being higher than the first temporal resolution.

Figure 16:
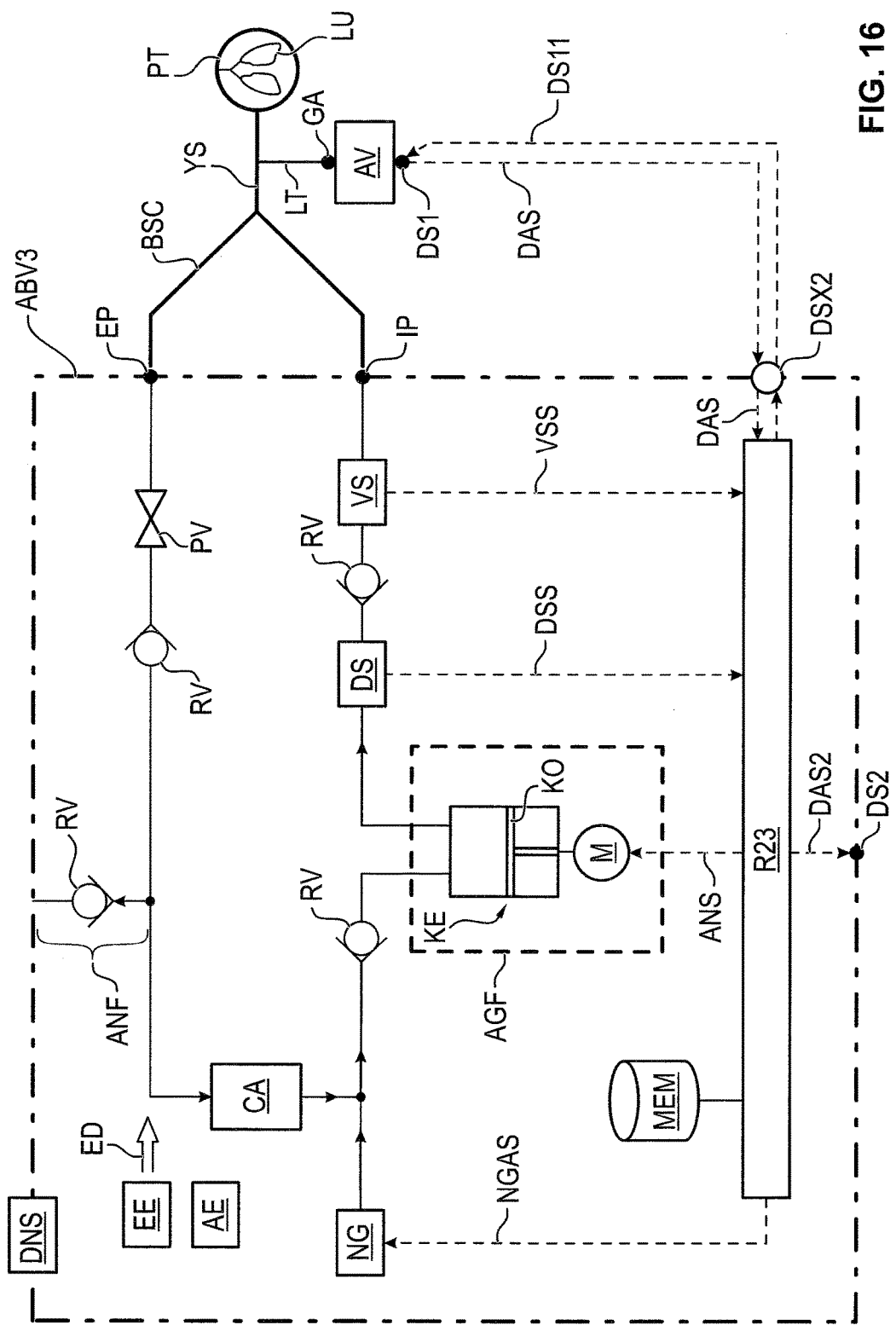
FIG. 16 is a schematic view of a first embodiment of an anesthesia ventilator.

A first embodiment of an anesthesia ventilator ABV3 is shown in FIG. 16.

FIG. 16 shows an anesthesia ventilator ABV3 for the automated ventilation of a patient PT. The anesthesia ventilator ABV3 has an inhalation port IP and an exhalation port EP, to which ports a ventilation tube BSC, which faces the patient PT, can be connected. An anesthesia ventilation gas is fed to the patient and also removed from the patient to the device ABV3 via this ventilation tube BSC. The feed is performed via the inhalation port IP, and the removal is performed via the exhalation port EP. The ventilation tube BSC merges the connections of the ports EP, IP at a so-called Y-piece YS, which then usually ends at a tube, which is inserted into the patient PT in order to ventilate him via his lungs LU.

The anesthesia ventilation device ABV3 further has a breathing gas feed unit AGF. The breathing gas feed unit AGF is preferably a piston unit KE, in which a piston KO can be moved forward and back by a motor M. The computing unit R is configured to actuate the breathing gas feed unit AGF via an actuating signal.

The anesthesia ventilator ABV3 has a volume flow sensor VS for detecting a volume flow of the breathing gas. The volume flow sensor VS can provide a volume flow sensor signal VSS for a computing unit R23.

The computing unit R23 is at least a computing unit that can also be embodied by a system comprising a plurality of computing units. The computing unit R23 is configured to perform a pressure-controlled or a pressure-assisted ventilation of the patient PT. The computing unit R23 preferably uses a memory unit MEM.

A minimum pressure (PEEP pressure) of the ventilation is brought about by a Peep valve PV, which is preferably located in the area of the exhalation port EP.

The anesthesia ventilator ABV3 further has a pressure sensor DS for detecting a pressure of the breathing gas. The pressure sensor DS provides a pressure sensor signal DSS for the computing unit R23.

The anesthesia ventilator ABV3 has a carbon dioxide absorber CA as well as an anesthetic-mixing unit NG. A gas mixture necessary for the anesthesia can then be introduced into the closed breathing circuit via the anesthetic-mixing unit NG. The anesthesia ventilator ABV3 further has an anesthetic gas discharge line ANF or a connection to an anesthetic gas discharge line ANF. The gas flow within the anesthesia ventilator ABV3 is preferably controlled by non-return valves RV. The computing unit R23 controls the anesthetic-mixing unit NG by means of a control signal NGAS.

The anesthesia ventilator ABV3 preferably has an input unit EE or an interface EE to an input unit, by means of which inputs, which are entered by an operator or clinician, can be made at the anesthesia ventilator ABV3.

The anesthesia ventilator ABV3 preferably has a display unit AE or an interface AE to a display unit AE, via which the determined concentration values can be displayed.

The anesthesia ventilator ABV3 further has a data interface DS2, at which the computing unit R23 provides a data signal DAS2, which indicates the determined concentration values.

Further, the anesthesia ventilator ABV3 preferably has a data network interface DNS, At which the computing unit R23 preferably provides the data signal DS2.

Via the input unit EE, the device ABV3 receives input data ED, which can be received at the computing unit R23.

These input data ED then predefine the selection of the respective time periods T1 and T2 of the respective operating modes BZ1 and BZ2, as is shown in FIG. 11. These input data ED can then be transmitted via a data signal DS11 via a data interface DSX2 of the device ABV3 to a device AV for the anesthetic gas measurement.

The device AV is either the device AV1 from FIG. 4 or the device AV2 from FIG. 5.

Via the data interface DS1 of the anesthetic gas analyzer AV, the anesthetic gas analyzer AV provides the concentration values of the types of anesthetic gases and preferably also the concentration values of the carbon dioxide measurement and/or of the dinitrogen monoxide measurement for the anesthesia ventilator ABV3 by means of a data signal DAS.

These values can then preferably be displayed on the display unit AE of the device ABV3.

The anesthetic gas analyzer AV has the gas port GA, as was already explained in reference to FIGS. 4 and 5, which can be coupled by means of a sample gas line LT with the Y-piece YS of the ventilation tube or can be connected there.

For an efficient gas feed of the anesthesia ventilation gas from the Y-piece YS to the anesthesia analyzer AV, it is possible that the anesthetic gas analyzer AV preferably has a pump of its own or can be connected to a pump.

The computing unit of the analyzer AV, which may be either the computing unit R from FIG. 4 or from FIG. 5, consequently receives the input data ED of the input unit EE by means of the data signal DS11 and then selects the maximum duration of the second operating mode as a function of these input data ED.

The device AV preferably has an input unit of its own or an interface of its own to an input unit in order to receive the input data ED.

Figure 17:
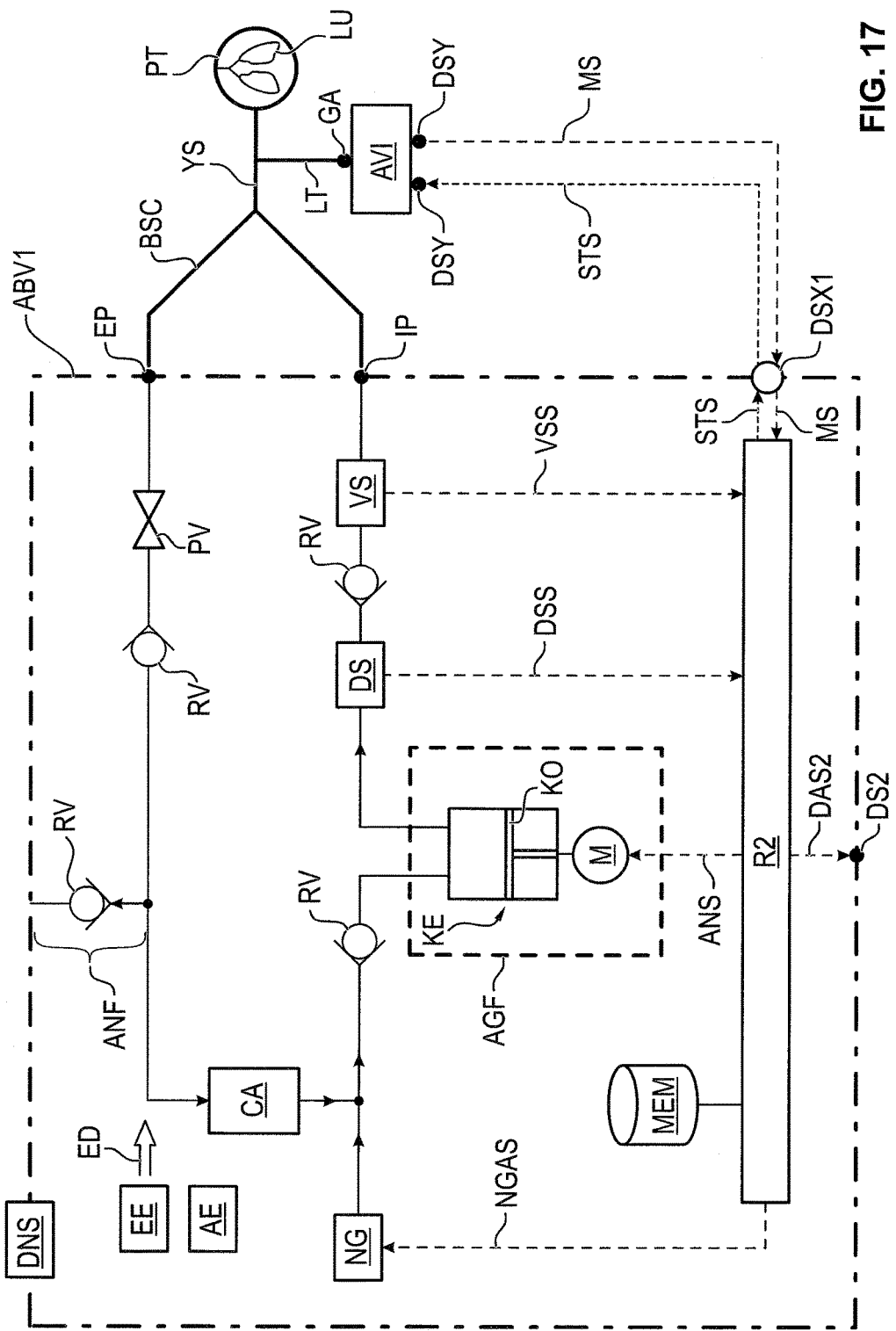
FIG. 17 is a schematic view of another embodiment of an anesthesia ventilator.

FIG. 17 shows another variant ABV1 for an anesthesia ventilator, in which an analyzer AVI is present instead of the analyzer AV from FIG. 16.

This analyzer AVI has interfaces DSY, by means of which a control signal STS as well as a measured signal MS can be exchanged. The control signal STS then corresponds to the control signal ST from FIG. 4 or from FIG. 5, The measured signal MS then corresponds at least to the measured signal MS1 from FIG. 4 or 5. The measured signal MS can further preferably have the second measured signal MS 100 or the second measured signal MS2. The anesthesia ventilator ABV1 has a data interface DSX1 for an exchange of these signals STS, MS.

The analyzer AVI is either the partial device AVI from FIG. 4 or alternatively the partial device AVI' from FIG. 5.

The functionalities of the computing unit R from FIG. 4 or from FIG. 5 are integrated here in the computing unit R2 of the anesthesia ventilator ABV1.

Compared to the embodiment of the anesthesia ventilator ABV3 from FIG. 16, the embodiment of the anesthesia ventilator ABV1 has the advantage that the analyzer AVI does not have to have a computing unit of its own, but the provision of the control signal STS as well as the detection of the measured signal MS and the further process from FIG. 6 can be provided or implemented by the computing unit R2 of the anesthesia ventilator ABV1, which said computing unit R2 is already present.

The analyzer AVI from FIG. 17 may preferably likewise have a pump for feeding the anesthesia ventilation gas from the Y-piece YS via the sample gas line LT to the analyzer AV1 or a connection to such a pump.

Figure 18:
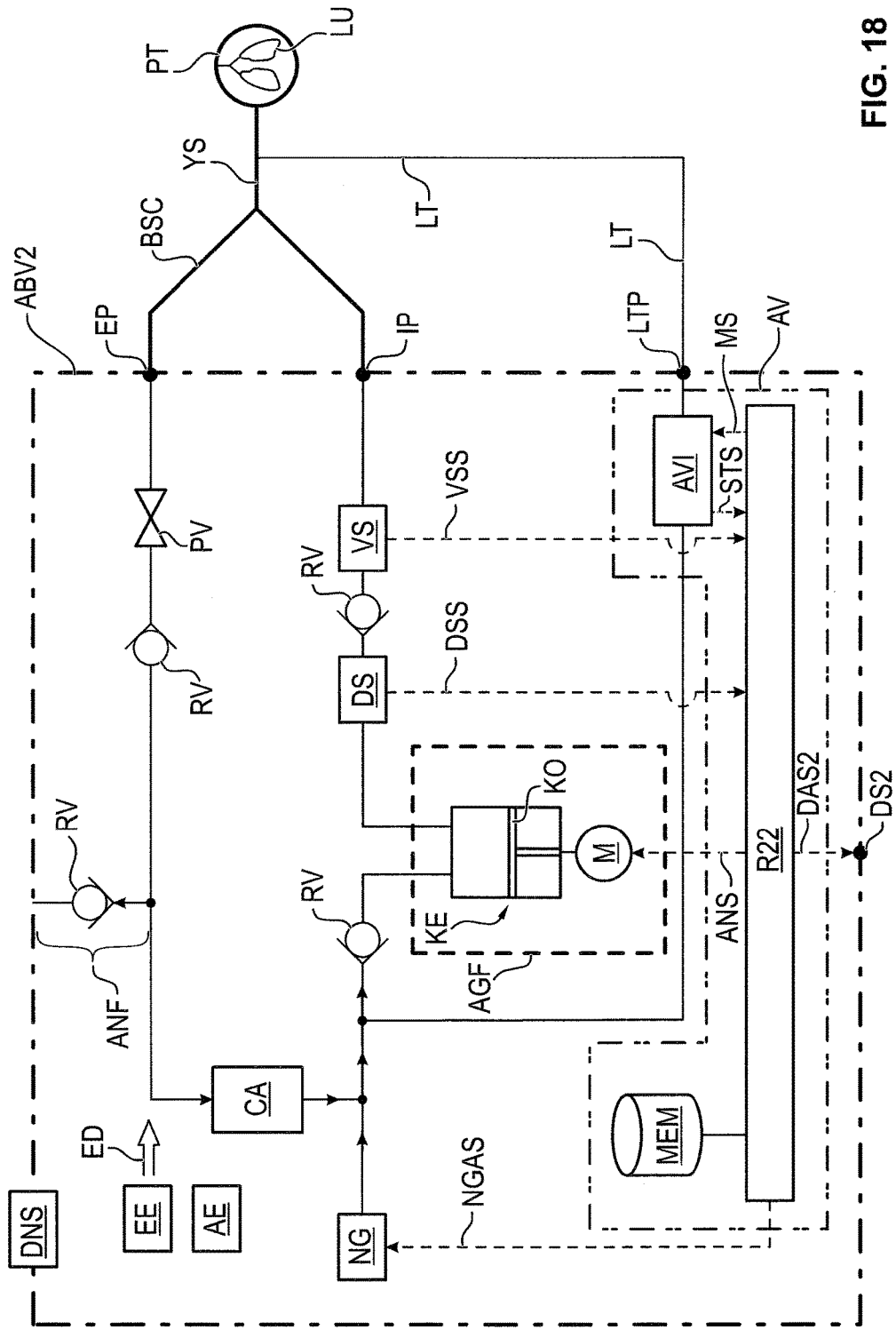
FIG. 18 is a schematic view of another embodiment of an anesthesia ventilator.

According to another embodiment ABV2 according to FIG. 18, an anesthesia ventilator has the analyzer AVI from FIG. 17 as an integral part. Here, the device ABV2 has the partial device AVI, which is preferably the partial device AVI from FIG. 4 or alternatively the partial device AVI' from FIG. 5. The analyzer AVI is coupled with the Y-piece YS by means of the sample gas line LT via a measured gas port or measured gas port LTP.

The computing unit R22 is configured here to provide the functionality of the computing unit R from FIG. 4 or from FIG. 5. The computing unit R22 is consequently configured for carrying out the determination step BS from FIG. 6.

The computing unit R22 is further configured to carry out functionalities that the computing unit R23 from FIG. 16 can perform. Further, the computing unit R2 from FIG. 17 is configured to carry out functionalities that the computing unit R23 from FIG. 16 can perform.

According to FIG. 4 and according to FIG. 5, the computing unit R of the embodiment AV1 or of the embodiment AV2 of the proposed device for the analysis of an anesthesia ventilation gas is further configured for providing another control signal ST2, by means of which the computing and control unit R2 modulates the amplitudes of the infrared radiation source SQ in the second operating mode according to a modulation frequency f_MOD. The computing and control unit R selects, in the first operating mode, the modulation frequency for this amplitude modulation as a function of the types of anesthetic gases detected as being present.

The computing and control unit R according to FIG. 4 or 5 consequently preferably performs an amplitude modulation of the radiation source SQ as a function of a modulation frequency f_MOD in the first operating mode.

This amplitude modulation is preferably effected by a sine signal of the modulation frequency f_MOD. As an alternative, an amplitude modulation by an ON/OFF keying is possible.

Figure 10C:
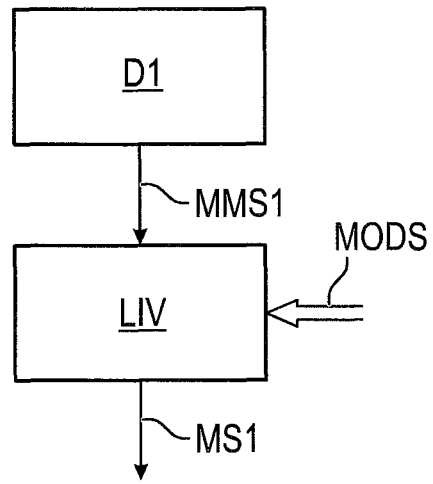
FIG. 10c is a flow diagram showing a demodulation of a signal received at a detector by means of a lock-in amplifier.

Consequently, a modulated measured signal MMS1, which is shown in FIG. 10c, is obtained instead of the measured signal MS1 at the detector D1 shown in FIGS. 4 and 5.

This modulated measured signal MMS1 is then sent to a so-called lock-in amplifier LIV, which carries out a demodulation according to a lock-in method, while providing a modulation signal MODS, which indicates the modulation frequency f_MOD used for the amplitude modulation of the radiation source SQ.

Thus, the first measured signal MS1 is then obtained behind the lock-in amplifier.

If the central transmission wavelength of the band pass filter function is adjusted, as is shown, for example, in FIG. 11 in the first operating mode, the frequency f_MOD must be adapted for the amplitude modulation to the change over time in the transmission wavelength TW from FIG. 11.

The modulation frequency f_MOD for the amplitude modulation must be higher here than a corresponding modulation frequency that is obtained from the change over time in the transmission wavelength TW.

Such a selection of the amplitude modulation frequency f_MOD is necessary for the amplitude modulation of the radiation source as a frequency that is higher than the modulation frequency of a frequency modulation that is obtained from the change over time in the transmission wavelength TW in the first operating mode because at least a plurality of periods of the amplitude modulation must pass through the band pass filter function of the Fabry-Perot interferometer at this fixed first transmission wavelength for an imaginary fixed value of the transmission wavelength TW.

Since infrared radiation sources, such as the radiation source SQ from FIGS. 4 and 5, can follow a modulation frequency for the amplitude modulation only conditionally, the effect may occur that the basic amplitude or the amplitude swing of the radiation source SQ decreases, as a result of which a signal-to-noise ratio may deteriorate.

If, for example, as is shown in FIG. 11, only an individual anesthetic gas was detected in the first operating mode BZ1, the transmission wavelength TW can then be selected, as was explained above, as a wavelength that is constant in time for the preferred wavelength WB1 during the second operating mode BZ2.

Since the first transmission wavelength TW can be maintained at a constant value as the wavelength WB1 during the second operating mode BZ2 in FIG. 11, there consequently is no change over time or even no change over time whatsoever in the first transmission wavelength TW during the second operating mode. Thus, the amplitude modulation of the radiation source SQ can then be carried out with a relatively low modulation frequency f_MOD.

If, as is shown in FIG. 12, a plurality of anesthetic gases are detected in the first operating mode BZ1, it is necessary to vary the central transmission wavelength TW over three preferred wavelengths, as was explained above, for an anesthetic gas measurement in the second operating mode BZ2. This greater variation over time in the central transmission wavelength TW in the case of a concentration measurement for two types of anesthetic gases compared to a variation over time in the central transmission wavelength TW in the case of a concentration measurement for only one anesthetic gas type, as was shown above in FIG. 11, consequently requires a higher modulation frequency f_MOD for the amplitude modulation.

The method of amplitude modulation makes possible an insensitivity or lower sensitivity to equisignal or DC components or also to a so-called 1/f noise.

Modulation of the radiation source according to an amplitude modulation does not necessarily have to be performed in the first operating mode BZ1. As an alternative, it is also possible to use a method in which such an amplitude modulation is simulated by means of an adjustment of the Fabry-Perot interferometer in this first operating mode, because the transfer function of the Fabry-Perot interferometer is not necessarily constant. This method is described in the document DE 10 2012 007 030 A1. However, the demodulation, which may be a lock-in method according to FIG. 10c by means of a lock-in amplifier LIV for an amplitude modulation, must now be replaced for the first operating mode by a method in which both a frequency modulation and an amplitude modulation of the central transmission wavelength occurs based on the method mentioned. Since the amplitude of the radiation source SQ according to FIG. 4 or 5 is not modulated here according to this method, a higher power can be tapped at the detector D1 or D2 than if an amplitude modulation of the radiation source SQ were necessary.

In the sense of this application, the aforementioned band pass filter functions BP1, . . . , BP5 of the Fabry-Perot interferometers FPI1, FPI2 shown in FIG. 4 or 5, which band pass filter functions are shown in FIG. 7, are variable band pass filter functions, which can be adjusted each in respect to their respective central transmission wavelengths TW, TW1, . . . , TW5 as a function of the control signal ST from FIGS. 4 and 5.

The computing and control unit R from FIGS. 4 and 5 is preferably embodied as an integrated hardware module, wherein one or more partial elements of such a computing and control unit R are programmable by software and/or have circuits which represent software. The partial elements of the at least one computing and control unit R are connected among one another for the exchange of data and/or signaling messages. The at least one computing and control unit R is not preferably embodied by an individual integrated hardware module, but by a plurality of hardware modules, which are connected to one another for the exchange of data and/or signaling messages, for example, by one or more bus systems. This also applies to the computing and control units R2, R22, R23 according to FIGS. 16, 17 and 18.

In other words, the function of the different computing and control units may consequently be embodied by corresponding hardware. This is preferably hardware that executes software in the form of program code. Such a unit maybe embodied in the form of an individual processor or of a system of a plurality of processors. The term "computing and control units" shall not be considered here exclusively to be pure hardware for executing software, but it may also be embodied as a digital signal processor (DSP), an Application Specific Integrated Circuit (ASIC), a Field Programmable Gate Array (FPGA) or as another type of hardware implementation.

The memory units ME, MEM mentioned in the exemplary embodiments may each be embodied by a single memory unit or by a plurality of memory units each. Such a memory unit or such memory units ME, MEM may be an integral part of a corresponding computing and control unit or units R, R2, R22 and R32.

While specific embodiments of the invention have been shown and described in detail to illustrate the application of the principles of the invention, it will be understood that the invention may be embodied otherwise without departing from such principles.

APPENDIX

List of Reference Designations

ABG Anesthesia ventilation gas
ABV1, ABV2, ABV3 Anesthesia ventilator
AD Analog-digital converter
AE Display unit
AGF Breathing gas feed unit
ANF Anesthetic gas discharge line
AV, AV1, AV2 Anesthetic gas analyzer
AVI, AVII, AVI', AVII' Partial device
BP1, . . . , BP5 Band pass filter function
BPF1, BPF2 Band pass filter
BPFF1, BPFF2 Fixed band pass filter function
BS Determination step
BSC Ventilation tube
BS1, . . . , BS7 Partial step
BS11, BS12, BS51, BS52, BS53, BS51' Substep
BZ1 First operating mode
BZ2 Second operating mode
CA Carbon dioxide absorber
DAS2 Data signal
DNS Data network interface
DS Pressure sensor
DSS Pressure signal
DSX1, DSX2, DS2, DS1 Data interface
DSY Interface
DUB Data set
ED Input data
EE Input unit
EP Exhalation port
FF1 Filter function
FOF Fixed optical filter
FPI1, FPI2 Fabry-Perot interferometer
FTW Fixed transmission wavelength
GK Gas cuvette
GP Ventilation gas sample
IP Inhalation port
KA, KC Concentration values
KE Piston unit
KO Piston
KV1, . . . , KV7 Absorbance curve
LIV Lock-in amplifier
LT Sample gas line
LTP Measuring gas port
LU Lungs
M Motor
ME, MEM Memory unit
MMS1 Modulated measured signal
MODS Modulation signal
MP1, MP2, MP3 Measurement point
MS1, MS2, MS100, MS Measured signal
MSD1, MSD2, MSD100 Digital measured signal
NG Anesthetic gas-mixing unit
NGAS Control signal
OF1, OF2 Optical device
PT Patient
PV Peep valve
R, R2, R22, R23 Computing unit
RV Nonreturn valve
S Infrared radiation
S1, S2, TS1, TS2 Intensity
SQ Infrared radiation source
ST, ST2 Control signal
STL Beam splitter
STS Control signal
T1, T2 Duration
TM1, TM2, TM3, TMA, TMB, TMC, TMI,
TMI', TMI", TMI1 Measurement time
TW, TW1, TW2, TW3 Central transmission wavelength
VS Volume flow sensor
VSS Volume flow signal
YS Y-piece
ZD Assignment data set
ZD1, . . . , ZD10 Partial data set
$\lambda 1, \lambda 2, \lambda 3, \lambda C, \lambda N$ Measuring wavelength
$\lambda R$ Reference wavelength
WB Wavelength range

What is claimed is:

1. A device for the analysis of anesthesia ventilation gas of an anesthesia ventilator, the device comprising:
at least one infrared radiation source for emission of infrared radiation along a measuring path;
at least one gas cuvette arranged in the measuring path for receiving a ventilation gas sample of anesthesia ventilation gas;
a Fabry-Perot interferometer arranged in the measuring path, the Fabry-Perot interferometer having a band pass filter means with a band pass central transmission wavelength that is adjustable as a function of a control signal;
at least one detector arranged at an end of a measuring path for providing a measured signal indicating an intensity of the radiation transmitted through the gas cuvette and through the band pass filter means of the Fabry-Perot interferometer;
at least one computing and control unit providing the control signal and detecting the measured signal, wherein the computing and control unit is further configured:
to actuate the Fabry-Perot interferometer, in a first operating mode, by the control signal such that the central transmission wavelength scans over a predefined wavelength range;
to detect, in the first operating mode, a respective presence in the ventilation gas sample for respective, potential types of anesthetic gases on the basis of the measured signal, and further;
to actuate the Fabry-Perot interferometer, in a second operating mode, by the control signal such that the central transmission wavelength corresponds to a preferred wavelength or to a plurality of preferred wavelengths within a subrange of the predefined wavelength range, wherein the computing and control unit selects the subrange as a function of types of anesthetic gases which were detected as being present in the first operating mode; and to determine a plurality of respective concentration values, in a second operating mode, at consecutive times for the respective types of anesthetic gases detected as being present on the basis of the measured signal.

2. A device in accordance with claim 1, wherein the computing and control unit selects the one preferred wavelength or the plurality of preferred wavelengths as a function of the types of anesthetic gases detected as being present.

3. A device in accordance with claim 1, wherein at least some of the types of anesthetic gases are fluranes.

4. A device in accordance with claim 1, wherein the predefined wavelength range, which scans the central transmission wavelength in the first operating mode, has at least a partial range of 8 µm to 9 µm.

5. A device in accordance with claim 1, wherein the computing and control unit selects the one preferred wavelength or the plurality of preferred wavelengths as a function of a data set, which data set indicates respective wavelength combinations or respective subranges for respective combinations of types of anesthetic gases.

6. A device in accordance with claim 2, wherein the computing and control unit selects the one preferred wavelength or the plurality of preferred wavelengths such that a type of anesthetic gas detected as being present has a predefined minimum of energy absorption of the infrared radiation at at least one of the preferred wavelengths.

7. A device in accordance with claim 1, wherein:
the Fabry-Perot interferometer has a plurality of band pass filter means, each of different orders;
the plurality of band pass filter means comprises a first band pass filter means of a first-type order with the central transmission wavelength as a first central transmission wavelength;
the plurality of band pass filter means further comprises an additional band pass filter means as a second band pass filter means of a second-type order with a second central transmission wavelength;
the detector comprises a first detector configured to provide a first measured signal, which indicates a first intensity of the infrared radiation, which first intensity corresponds to infrared radiation that was transmitted through the gas cuvette and through the first band pass filter means of the Fabry-Perot interferometer;
the detector further comprises a second detector arranged at the end of the measuring path and which is configured to provide a second measured signal, which second measured signal indicates a second intensity of the infrared radiation, which second intensity corresponds to infrared radiation that was transmitted through the gas cuvette and through the second band pass filter means of the Fabry-Perot interferometer;
the computing and control unit is further configured to actuate the Fabry-Perot interferometer in the second operating mode by means of the control signal such that the second central transmission wavelength corresponds at least at times to additional preferred wavelengths between 4 µm and 5 µm; and
the computing and control unit is further configured to determine a plurality of concentration values at a plurality of consecutive times for carbon dioxide on the basis of the second measured signal.

8. A device in accordance with claim 1, further comprising at least one fixed optical filter comprising a fixed band pass filter with a fixed central transmission wavelength between 4 µm and 5 µm, wherein:
the detector comprises a first detector configured to provide a first measured signal, which first measured signal indicates a first intensity of the infrared radiation, which first intensity corresponds to infrared radiation that is passed through the gas cuvette and through the band pass filter of the Fabry-Perot interferometer;
the detector further comprises a second detector arranged at the end of the measuring path and which is configured to provide a second measured signal, which second measured signal indicates a second intensity of the infrared radiation, which second intensity corresponds to infrared radiation that is transmitted through the gas cuvette and through the fixed band pass filter of the fixed optical filter; and
the computing and control unit is further configured to determine a plurality of concentration values for carbon dioxide at a plurality of consecutive times at least in the second operating mode on based on the second measured signal.

9. A device in accordance with claim 1, further comprising a data interface, wherein the computing and control unit is configured to provide the concentration values at the data interface.

10. A device in accordance with claim 1, further comprising a gas port for feeding the ventilation gas sample of the anesthesia ventilation gas.

11. A device in accordance with claim 10, wherein the gas port is configured for connection to a Y-piece of a ventilation tube.

12. A device in accordance with claim 1, wherein the computing and control unit is configured to change back over into the first operating mode from the second operating mode at the latest after an end of a maximum duration of the second operating mode.

13. A device in accordance with claim 12, wherein the computing and control unit is configured to receive input data of an input unit and further to select the maximum duration of the second operating mode as a function of the input data.

14. A device in accordance with claim 1, wherein:
the computing and control unit is configured to modulate the amplitude of the infrared radiation source in the first operating mode by means of an additional control signal according to a modulation frequency;
the computing and control unit selects the modulation frequency as a function of the types of anesthetic gases detected as being present from the first operating mode.

15. An anesthesia ventilator comprising an anesthesia ventilation gas flow path and a gas analysis device comprising:
at least one infrared radiation source for emission of infrared radiation along a measuring path;
at least one gas cuvette arranged in the measuring path for receiving a ventilation gas sample of anesthesia ventilation gas;
a Fabry-Perot interferometer arranged in the measuring path, the Fabry-Perot interferometer having a band pass filter means with a band pass central transmission wavelength that is adjustable as a function of a control signal;
at least one detector arranged at an end of a measuring path for providing a measured signal indicating an intensity of the radiation transmitted through the gas cuvette and through the band pass filter means of the Fabry-Perot interferometer;
at least one computing and control unit providing the control signal and detecting the measured signal, wherein the computing and control unit is further configured:

to actuate the Fabry-Perot interferometer, in a first operating mode, by the control signal such that the central transmission wavelength scans over a predefined wavelength range;

to detect, in the first operating mode, a respective presence in the ventilation gas sample for respective, potential types of anesthetic gases on the basis of the measured signal, and further;

to actuate the Fabry-Perot interferometer, in a second operating mode, by the control signal such that the central transmission wavelength corresponds to a preferred wavelength or to a plurality of preferred wavelengths within a subrange of the predefined wavelength range, wherein the computing and control unit selects the subrange as a function of types of anesthetic gases which were detected as being present in the first operating mode; and to determine a plurality of respective concentration values, in a second operating mode, at consecutive times for the respective types of anesthetic gases detected as being present on the basis of the measured signal.

16. An anesthesia ventilator in accordance with claim 15, wherein the computing and control unit selects the one preferred wavelength or the plurality of preferred wavelengths as a function of a data set, which data set indicates respective wavelength combinations or respective subranges for respective combinations of types of anesthetic gases.

17. An anesthesia ventilator in accordance with claim 15, wherein the computing and control unit selects the one preferred wavelength or the plurality of preferred wavelengths as a function of the types of anesthetic gases detected as being present such that a type of anesthetic gas detected as being present has a predefined minimum of energy absorption of the infrared radiation at at least one of the preferred wavelengths.

18. An anesthesia ventilator in accordance with claim 15, wherein:

the Fabry-Perot interferometer has a plurality of band pass filter means, each of different orders;

the plurality of band pass filter means comprises a first band pass filter means of a first-type order with the central transmission wavelength as a first central transmission wavelength;

the plurality of band pass filter means further comprises an additional band pass filter means as a second band pass filter means of a second-type order with a second central transmission wavelength;

the detector comprises a first detector configured to provide a first measured signal, which indicates a first intensity of the infrared radiation, which first intensity corresponds to infrared radiation that was transmitted through the gas cuvette and through the first band pass filter means of the Fabry-Perot interferometer;

the detector further comprises a second detector arranged at the end of the measuring path and which is configured to provide a second measured signal, which second measured signal indicates a second intensity of the infrared radiation, which second intensity corresponds to infrared radiation that was transmitted through the gas cuvette and through the second band pass filter means of the Fabry-Perot interferometer;

the computing and control unit is further configured to actuate the Fabry-Perot interferometer in the second operating mode by means of the control signal such that the second central transmission wavelength corresponds at least at times to additional preferred wavelengths between 4 µm and 5 µm; and the computing and control unit is further configured to determine a plurality of concentration values at a plurality of consecutive times for carbon dioxide on the basis of the second measured signal.

19. An anesthesia ventilator in accordance with claim 15, further comprising at least one fixed optical filter comprising a fixed band pass filter with a fixed central transmission wavelength between 4 µm and 5 µm, wherein:

the detector comprises a first detector configured to provide a first measured signal, which first measured signal indicates a first intensity of the infrared radiation, which first intensity corresponds to infrared radiation that is passed through the gas cuvette and through the band pass filter of the Fabry-Perot interferometer;

the detector further comprises a second detector arranged at the end of the measuring path and which is configured to provide a second measured signal, which second measured signal indicates a second intensity of the infrared radiation, which second intensity corresponds to infrared radiation that is transmitted through the gas cuvette and through the fixed band pass filter of the fixed optical filter; and the computing and control unit is further configured to determine a plurality of concentration values for carbon dioxide at a plurality of consecutive times at least in the second operating mode on based on the second measured signal.

20. An anesthesia ventilator comprising a computing and control unit for the analysis of an anesthesia ventilation gas, wherein the computing and control unit is configured to provide a control signal and further to detect a measured signal, wherein the computing and control unit is further configured:

to actuate a Fabry-Perot interferometer, in a first operating mode, with the control signal such that a central transmission wavelength of a band pass filter means of the Fabry-Perot interferometer scans a predefined wavelength range; and to detect a respective presence in a ventilation gas sample of the anesthesia ventilation gas, in a first operating mode, for respective, potential types of anesthetic gases on the basis of the measured signal;

to actuate the Fabry-Perot interferometer, in a second operating mode, with the control signal such that the central transmission wavelength corresponds to a preferred wavelength or to a plurality of preferred wavelengths within a subrange of the predefined wavelength range, wherein the computing and control unit selects the subrange as a function of types of anesthetic gases detected as being present; and to determine a plurality of respective concentration values at a plurality of consecutive times, in a second operating mode, based on of the measured signal for the respective types of anesthetic gases detected as being present.

* * * * *